United States Patent
Drew et al.

(10) Patent No.: US 9,259,177 B2
(45) Date of Patent: *Feb. 16, 2016

(54) TECHNIQUES FOR DATA RETENTION UPON DETECTION OF AN EVENT IN AN IMPLANTABLE MEDICAL DEVICE

(71) Applicant: Medtronic, Inc., Minneapolis, MN (US)

(72) Inventors: Touby A. Drew, Minneapolis, MN (US); Jonathon E. Giftakis, Maple Grove, MN (US); David L. Carlson, Fridley, MN (US); Eric J. Panken, Edina, MN (US); Jonathan C. Werder, Corcoran, MN (US); Nina M. Graves, Minnetonka, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/452,312

(22) Filed: Aug. 5, 2014

(65) Prior Publication Data

US 2015/0080674 A1    Mar. 19, 2015

Related U.S. Application Data

(63) Continuation of application No. 14/039,612, filed on Sep. 27, 2013, now Pat. No. 8,798,728, which is a continuation of application No. 13/349,404, filed on Jan. 12, 2012, now Pat. No. 8,565,864, which is a (Continued)

(51) Int. Cl.
*A61B 5/024* (2006.01)
*A61B 5/00* (2006.01)

(Continued)

(52) U.S. Cl.
CPC .............. *A61B 5/4094* (2013.01); *A61B 5/0006* (2013.01); *A61B 5/0031* (2013.01);

(Continued)

(58) Field of Classification Search
USPC .......................................... 600/513
See application file for complete search history.

(56) References Cited

U.S. PATENT DOCUMENTS

| 3,958,563 A | 5/1976 | Fernandez |
| 4,228,806 A | 10/1980 | Lidlow |

(Continued)

FOREIGN PATENT DOCUMENTS

| EP | 0554208 | 8/1993 |
| EP | 1269911 | 1/2003 |
| WO | WO2004/023983 | 3/2004 |

OTHER PUBLICATIONS

PCT/US2005/039478: International Preliminary Report on Patentability dated May 18, 2007.

(Continued)

*Primary Examiner* — Paula J Stice
(74) *Attorney, Agent, or Firm* — Withers & Keys, LLC

(57) ABSTRACT

Methods and apparatus for storing data records associated with a medical monitoring event in a data structure. These include initiating loop recording in an implantable medical device upon determination of a neurological event, wherein loop recording comprises storing a data record of a plurality of data records in a data structure, the plurality of data records representing information about determined neurological events. Methods and apparatus can further include determining a priority index for the plurality of data records based on severity levels of the determined neurological events and replacing older data records of the plurality of data records on the data structure with new data records according to the priority index, wherein the new data records selectively replace those data records in the data structure having the lowest associated priority index.

15 Claims, 20 Drawing Sheets

Related U.S. Application Data continuation of application No. 11/264,974, filed on Nov. 2, 2005, now Pat. No. 8,108,033.

(60) Provisional application No. 60/624,232, filed on Nov. 2, 2004.

(51) Int. Cl.

| | | |
|---|---|---|
| *A61B 5/04* | (2006.01) | |
| *A61N 1/372* | (2006.01) | |
| *G06F 19/00* | (2011.01) | |
| *G06F 17/30* | (2006.01) | |
| *A61B 5/0205* | (2006.01) | |
| *A61B 5/0402* | (2006.01) | |
| *A61B 5/0476* | (2006.01) | |
| *A61B 5/11* | (2006.01) | |
| *A61B 5/16* | (2006.01) | |
| *A61N 1/36* | (2006.01) | |
| *A61N 1/365* | (2006.01) | |
| *A61N 1/37* | (2006.01) | |
| *A61B 5/021* | (2006.01) | |
| *A61B 5/03* | (2006.01) | |
| *A61B 5/08* | (2006.01) | |

(52) U.S. Cl.
CPC ......... *A61B5/02055* (2013.01); *A61B 5/04001* (2013.01); *A61B 5/0402* (2013.01); *A61B 5/04012* (2013.01); *A61B 5/0476* (2013.01); *A61B 5/1118* (2013.01); *A61B 5/165* (2013.01); *A61B 5/4082* (2013.01); *A61B 5/686* (2013.01); *A61B 5/7282* (2013.01); *A61N 1/36135* (2013.01); *A61N 1/37252* (2013.01); *G06F 17/30336* (2013.01); *G06F 19/322* (2013.01); *G06F 19/3418* (2013.01); *A61B 5/021* (2013.01); *A61B 5/024* (2013.01); *A61B 5/031* (2013.01); *A61B 5/0816* (2013.01); *A61B 5/7232* (2013.01); *A61N 1/36132* (2013.01); *A61N 1/36521* (2013.01); *A61N 1/36585* (2013.01); *A61N 1/3702* (2013.01); *A61N 1/37282* (2013.01); *G06F 19/3406* (2013.01)

(56) References Cited

U.S. PATENT DOCUMENTS

| | | | |
|---|---|---|---|
| 4,374,382 A | 2/1983 | Markowitz | |
| 4,485,813 A | 12/1984 | Anderson | |
| 4,556,063 A | 12/1985 | Thompson | |
| 4,567,892 A | 2/1986 | Plicchi | |
| 4,583,553 A | 4/1986 | Shah | |
| 4,596,251 A | 6/1986 | Plicchi | |
| 4,903,701 A | 2/1990 | Moore | |
| 4,920,489 A | 4/1990 | Hubelbank | |
| 4,945,477 A | 7/1990 | Edwards | |
| 5,007,431 A | 4/1991 | Donchoo, III | |
| 5,012,411 A | 4/1991 | Policastro | |
| 5,052,388 A | 10/1991 | Sivula | |
| 5,078,134 A | 1/1992 | Heilman | |
| 5,127,404 A | 7/1992 | Wyborny | |
| 5,168,759 A | 12/1992 | Bowman | |
| 5,215,086 A | 6/1993 | Terry, Jr. | |
| 5,269,302 A | 12/1993 | Swartz | |
| 5,285,792 A | 2/1994 | Sjoquist | |
| 5,312,446 A | 5/1994 | Holschbach | |
| 5,336,244 A | 8/1994 | Weijand | |
| 5,354,318 A | 10/1994 | Taepke | |
| 5,409,009 A | 4/1995 | Olson | |
| 5,431,691 A | 7/1995 | Snell | |
| 5,439,481 A | 8/1995 | Adams | |
| 5,518,001 A | 5/1996 | Snell | |
| 5,554,177 A | 9/1996 | Kieval | |
| 5,645,068 A | 7/1997 | Mezack et al. | |
| 5,659,614 A | 8/1997 | Bailey, III | |
| 5,722,999 A | 3/1998 | Snell | |
| 5,726,898 A | 3/1998 | Jacobs | |
| 5,732,708 A | 3/1998 | Nau | |
| 5,752,976 A | 5/1998 | Duffin | |
| 5,776,168 A | 7/1998 | Gunderson | |
| 5,782,891 A | 7/1998 | Hassler | |
| 5,790,427 A | 8/1998 | Greer | |
| 5,891,043 A | 4/1999 | Ericksen | |
| 5,899,866 A | 5/1999 | Cyrus | |
| 5,908,392 A | 6/1999 | Wilson | |
| 5,944,745 A | 8/1999 | Rueter | |
| 5,987,352 A | 11/1999 | Klein | |
| 5,995,868 A | 11/1999 | Dorfmeister | |
| 5,995,874 A | 11/1999 | Borza | |
| 6,016,449 A | 1/2000 | Fischell | |
| 6,061,593 A | 5/2000 | Fischell | |
| 6,067,473 A | 5/2000 | Greeninger | |
| 6,128,538 A | 10/2000 | Fischell | |
| 6,134,474 A | 10/2000 | Fischell | |
| 6,161,043 A | 12/2000 | McClure | |
| 6,200,265 B1 | 3/2001 | Walsh et al. | |
| 6,227,203 B1 | 5/2001 | Rise | |
| 6,329,139 B1 | 12/2001 | Nova | |
| 6,360,122 B1 | 3/2002 | Fischell et al. | |
| 6,364,834 B1 | 4/2002 | Reuss et al. | |
| 6,405,086 B1 | 6/2002 | Conley | |
| 6,427,086 B1 | 7/2002 | Fischell | |
| 6,438,649 B1 | 8/2002 | Tanaka | |
| 6,456,887 B1 | 9/2002 | Dudding et al. | |
| 6,496,715 B1 | 12/2002 | Lee | |
| 6,505,067 B1 | 1/2003 | Lee | |
| 6,512,940 B1 | 1/2003 | Brabec | |
| 6,522,915 B1 | 2/2003 | Ceballos | |
| 6,526,314 B1 | 2/2003 | Eberle | |
| 6,549,804 B1 | 4/2003 | Osorio | |
| 6,577,901 B2 | 6/2003 | Thompson | |
| 6,589,187 B1 | 7/2003 | Dirnberger et al. | |
| 6,599,242 B1 | 7/2003 | Splett | |
| 6,611,714 B1 | 8/2003 | Mo | |
| 6,628,985 B2 | 9/2003 | Sweeney | |
| 6,647,296 B2 | 11/2003 | Fischell | |
| 6,662,049 B1 | 12/2003 | Miller | |
| 6,664,729 B2 | 12/2003 | Elledge | |
| 6,684,106 B2 | 1/2004 | Herbst | |
| 6,700,869 B1 | 3/2004 | Falco et al. | |
| 6,704,595 B2 | 3/2004 | Bardy | |
| 6,721,490 B1 | 4/2004 | Yao et al. | |
| 6,803,798 B1 | 10/2004 | Wei | |
| 6,823,210 B2 | 11/2004 | Eberle | |
| 6,904,311 B2 | 6/2005 | Freeberg | |
| 6,907,289 B2 | 6/2005 | Stahmann | |
| 7,079,977 B2 | 7/2006 | Osorio et al. | |
| 7,089,056 B2 | 8/2006 | Koshiol | |
| 7,130,678 B2 | 10/2006 | Ritscher et al. | |
| 7,212,858 B2 | 5/2007 | Schaldach | |
| 7,280,867 B2 | 10/2007 | Frei | |
| 7,285,090 B2 | 10/2007 | Stivoric | |
| 7,313,440 B2 | 12/2007 | Miesel | |
| 7,392,090 B2 | 6/2008 | Sweeney | |
| 7,450,743 B2 | 11/2008 | Sundar | |
| 7,460,904 B2 | 12/2008 | Deadwyler | |
| 7,496,403 B2 | 2/2009 | Cao | |
| 7,515,961 B2 | 4/2009 | Germanson | |
| 7,668,591 B2 | 2/2010 | Lee | |
| 7,756,573 B2 | 7/2010 | Shen et al. | |
| 7,917,199 B2 | 3/2011 | Drew | |
| 8,024,029 B2 | 9/2011 | Drew | |
| 8,108,033 B2 * | 1/2012 | Drew et al. | 600/509 |
| 8,224,431 B2 | 7/2012 | Drew | |
| 8,478,417 B2 | 7/2013 | Drew | |
| 8,565,864 B2 * | 10/2013 | Drew et al. | 600/509 |
| 8,768,446 B2 | 7/2014 | Drew | |
| 8,798,728 B2 * | 8/2014 | Drew et al. | 600/509 |
| 2001/0051819 A1 | 12/2001 | Fischell | |
| 2002/0013614 A1 | 1/2002 | Thompson | |
| 2002/0077563 A1 | 6/2002 | Sweeney | |

(56) References Cited

U.S. PATENT DOCUMENTS

| | | |
|---|---|---|
| 2002/0099303 A1 | 7/2002 | Bardy |
| 2002/0198473 A1 | 12/2002 | Kumar et al. |
| 2003/0074033 A1 | 4/2003 | Pless et al. |
| 2003/0174069 A1 | 9/2003 | Goetz et al. |
| 2003/0187365 A1 | 10/2003 | Eberle |
| 2004/0059391 A1 | 3/2004 | Sweeney |
| 2004/0077563 A1 | 4/2004 | Lau |
| 2004/0122296 A1 | 6/2004 | Hatlestad et al. |
| 2004/0122331 A1 | 6/2004 | Freeberg |
| 2004/0122706 A1 | 6/2004 | Walker et al. |
| 2004/0127945 A1 | 7/2004 | Collins et al. |
| 2004/0133390 A1 | 7/2004 | Osorio |
| 2004/0138536 A1 | 7/2004 | Frei et al. |
| 2004/0138579 A1 | 7/2004 | Deadwyler et al. |
| 2004/0152957 A1 | 8/2004 | Stivoric |
| 2004/0183579 A1 | 9/2004 | Wei |
| 2004/0215270 A1 | 10/2004 | Ritscher et al. |
| 2005/0027324 A1 | 2/2005 | Schaldach |
| 2005/0081847 A1 | 4/2005 | Lee et al. |
| 2005/0203366 A1 | 9/2005 | Donoghue et al. |
| 2005/0203385 A1 | 9/2005 | Sundar |
| 2005/0209524 A1 | 9/2005 | Donaldson |
| 2005/0222631 A1 | 10/2005 | Dalal |
| 2006/0095092 A1 | 5/2006 | Drew |
| 2006/0247706 A1 | 11/2006 | Germanson |
| 2007/0049982 A1 | 3/2007 | Cao |
| 2007/0208232 A1 | 9/2007 | Kovacs |
| 2007/0255151 A1 | 11/2007 | Struble |
| 2012/0116183 A1 | 5/2012 | Osorio |

OTHER PUBLICATIONS

PCT/US2005/039478: Search Report and Written Opinion dated Apr. 3, 2006.
PCT/US2005/039857: International Preliminary Report on Patentability dated Jan. 19, 2008.
PCT/US2005/039857: Search Report and Written Opinion dated Apr. 25, 2006.
PCT/US2005/040190: Corrected International Search Report and Written Opinion dated May 2, 2006.
PCT/US2005/040190: International Preliminary Report on Patentability dated May 8, 2007.
PCT/US2005/040192: International Preliminary Report on Patentability dated Jan. 19, 2007.
PCT/US2005/040192: Search Report and Written Opinion, dated Apr. 25, 2006.
PCT/US2005/040193: International Preliminary Report on Patentability dated Jan. 15, 2007.
PCT/US2005/040193: Search Report and Written Opinion, dated May 8, 2006.
PCT/US2005/040194: International Preliminary Report on Patentability dated May 18, 2007.
PCT/US2005/040194: Search Report and Written Opinion dated May 4, 2006.

\* cited by examiner

TECHNIQUES FOR DATA RETENTION UPON DETECTION OF AN EVENT IN AN IMPLANTABLE MEDICAL DEVICE

RELATED APPLICATIONS

This patent application is a continuation of U.S. patent application Ser. No. 14/039,612, filed Sep. 27, 2013, now U.S. Pat. No. 8,798,728, which is a continuation of U.S. patent application Ser. No. 13/349,404, filed Jan. 12, 2012, now U.S. Pat. No. 8,565,864, which is a continuation of U.S. patent application Ser. No. 11/264,974, filed Nov. 2, 2005, now U.S. Pat. No. 8,108,033, which claims priority to U.S. Provisional Patent Application Ser. No. 60/624,232, filed Nov. 2, 2004, all of which are incorporated herein in their entireties.

FIELD OF THE INVENTION

The invention relates to techniques for selecting, storing and reporting data associated with physiologic signals that may be further associated with a neurological event.

BACKGROUND OF THE INVENTION

Nervous system disorders affect millions of people, causing death and a degradation of life. Nervous system disorders include disorders of the central nervous system, peripheral nervous system, and mental health and psychiatric disorders. Such disorders include, for example without limitation, epilepsy, Parkinson's disease, essential tremor, dystonia, headache, and multiple sclerosis (MS). Additionally, nervous system disorders include mental health disorders and psychiatric disorders which also affect millions of individuals and include, but are not limited to, anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (narcolepsy), obesity, and anorexia.

As an example, epilepsy is the most prevalent serious neurological disease across all ages. Epilepsy is a group of neurological conditions in which a person has or is predisposed to recurrent seizures. A seizure is a clinical manifestation resulting from excessive, hypersynchronous, abnormal electrical or neuronal activity in the brain. (A neurological event is an activity that is indicative of a nervous system disorder. A seizure is a type of a neurological event.) This electrical excitability of the brain may be likened to an intermittent electrical overload that manifests with sudden, recurrent, and transient changes of mental function, sensations, perceptions, and/or involuntary body movement. Because the seizures are unpredictable, epilepsy affects a person's employability, psychosocial life, and ability to operate vehicles or power equipment. It is a disorder that occurs in all age groups, socioeconomic classes, cultures, and countries. In developed countries, the age-adjusted incidence of recurrent unprovoked seizures ranges from 24/100,000 to 53/100,000 person-years and may be even higher in developing countries. In developed countries, age specific incidence is highest during the first few months of life and again after age 70. The age-adjusted prevalence of epilepsy is 5 to 8 per 1,000 (0.5% to 0.8%) in countries where statistics are available. In the United States alone, epilepsy and seizures affect 2.3 million Americans, with approximately 181,000 new cases occurring each year. It is estimated that 10% of Americans will experience a seizure in their lifetimes, and 3% will develop epilepsy by age 75.

There are various approaches in treating nervous system disorders. Treatment therapies can include any number of possible modalities alone or in combination including, for example, electrical stimulation, magnetic stimulation, drug infusion, and/or brain temperature control. Each of these treatment modalities can be operated using closed-loop feedback control. Such closed-loop feedback control techniques receive from a monitoring element a neurological signal that carries information about a symptom or a condition or a nervous system disorder. Such a neurological signal can include, for example, electrical signals (such as EEG, ECoG, and/or EKG), chemical signals, other biological signals (such as change in quantity of neurotransmitters), temperature signals, pressure signals (such as blood pressure, intracranial pressure or cardiac pressure), respiration signals, heart rate signals, pH-level signals, and peripheral nerve signals (cuff electrodes on a peripheral nerve). Monitoring elements can include, for example, recording electrodes or various types of sensors.

For example, U.S. Pat. No. 5,995,868 discloses a system for the prediction, rapid detection, warning, prevention, or control of changes in activity states in the brain of a patient. Use of such a closed-loop feed back system for treatment of a nervous system disorder may provide significant advantages in that treatment can be delivered before the onset of the symptoms of the nervous system disorder.

During the operation of a medical device system, the patient is likely to experience multiple detections of the nervous system disorder. For example, in the case of seizures, the patient may have thousands of seizures over the course of a time period, but only a few will have behavioral manifestations. The other seizure episodes that don't exhibit behavioral manifestations are considered sub-clinical or electrographic seizures. When the medical device system monitors for seizure occurrences, however, the medical device system will detect many seizure events although only some of these events will spread to other parts of the brain such that the patient will exhibit it (e.g., convulsions, unconsciousness, etc.).

In order to effectively provide treatment therapy, an implanted device may be required to record physiologic data that is related to the disorder. However, an implanted device is typically limited by memory capacity and by battery capacity. Thus, the implanted device is limited in the amount of data that can be stored and reported.

An implanted device often stores physiologic data in a data structure and manages memory allocation for the data structure. However, the memory allocation management supported by the implanted device may have deficiencies. For example, with a FIFO memory buffer if the amount of collected physiologic data exceeds the available memory space, the oldest physiologic data is lost regardless of the importance of the lost data.

It is therefore desirable to selectively store physiologic data in a limited memory space of an implanted device. The implanted device can report the most relevant data from the stored data so that the implanted device can be configured to provide efficacious treatment.

BRIEF SUMMARY

The following represents a simplified summary of some embodiments of the invention in order to provide a basic understanding of various aspects of the invention. This summary is not an extensive overview of the invention nor is it intended to identify key or critical elements of the invention or to delineate the scope of the invention. Its sole purpose is to present some embodiments of the invention in simplified form as a prelude to the more detailed description that is presented thereafter.

In accordance with an aspect of the invention, data records associated with a physiologic event, e.g., a neurological event, are stored in memory that includes first data structure and a second structure. Upon detection of a possible occurrence of a physiological event by one group of monitoring elements, an implanted device records data received from another group of monitoring elements. The implanted device obtains acquired data and stores a data record associated with the data in a selected data entry of the first data structure (e.g., an age buffer such as circular buffer). Before an older data record in the first data structure is replaced (completely or partially) with a new data record, the older data record may stored in the second data structure if the associated priority index exceeds a threshold criterion e.g., exceeds a predetermined threshold value and/or is larger than a corresponding priority index of any data record that is currently stored in the second data structure). With another embodiment of the invention, the older data record may be stored in a min-max heap in accordance with the associated priority index.

In accordance with another aspect of the invention, the priority index that is associated with a data record may be determined by the severity level of a physiologic event and may be further determined by associated factors that may include associated physiologic events.

In accordance with another aspect of the invention, in response to an instruction from a clinician, an implanted device organizes stored physiologic data according to the associated priority index and reports a predetermined number of data records that are deemed as having a higher priority index than the other stored data records.

In accordance with another aspect of the invention, a subset or a composite of physiologic channels is selected from the available physiologic channels based on a selection criterion. The subset of physiologic channels may be processed and/or stored by an implanted device.

DETAILED DESCRIPTION OF THE INVENTION

Figure 1:
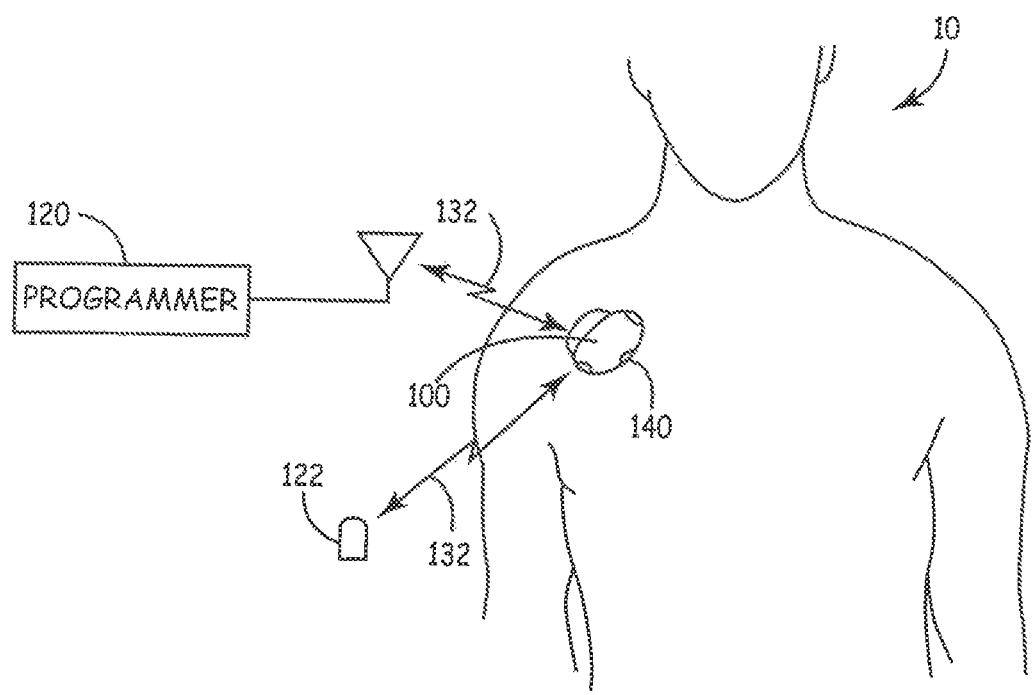
FIG. 1 is a simplified schematic view of a thoracic cavity leadless medical device implanted in a patient that monitors cardiac and respiratory parameters in accordance with an embodiment of the invention.

The following description discloses techniques for selecting, storing and reporting data associated with physiologic signals that may be further associated with a neurological event. These techniques are suitable for use within any implantable medical device system including, but not limited to, a core monitoring device, a full monitoring device, and/or a combination monitoring and treatment device (e.g., involving brain, respiration, and/or cardiac physiologic signals, discussed below). For example, a core monitor system may consist of ECG and respiratory inputs, a full monitor system may consist of ECG, respiratory and EEG inputs, a monitor/treatment system may include brain, cardiac inputs and phrenic nerve stimulation various combinations.

In an embodiment, the invention is implemented within an implantable neurostimulator system, however, as already discussed, those skilled in the art will appreciate that the techniques disclosed herein may be implemented generally within any implantable medical device system having monitoring capabilities of physiological conditions of the patient including, but not limited to, implantable drug delivery systems, implantable systems providing stimulation and drug delivery, pacemaker systems, defibrillator systems, cochlear implant systems, and implantable diagnostic system for detecting bodily conditions, including those in organs like the brain and/or the heart. The implantable medical device may provide therapeutic treatment to neural tissue in any number of locations in the body including, for example, the brain (which includes the brain stem), the vagus nerve, the spinal cord, peripheral nerves, etc. The treatment therapies can include any number of possible modalities alone or in combination including, for example, electrical stimulation, magnetic stimulation, drug infusion, brain temperature control, and/or any combination thereof.

In addition, the invention may be embodied in various forms to analyze and treat nervous system and other disorders, namely disorders of the central nervous system, peripheral nervous system, and mental health and psychiatric disorders. Such disorders include, for example without limitation, epilepsy, Sudden Unexpected Death in Epilepsy Patients (SUDEP), Parkinson's disease, essential tremor, dystonia, multiple sclerosis (MS), anxiety (such as general anxiety, panic, phobias, post traumatic stress disorder (PTSD), and obsessive compulsive disorder (OCD)), mood disorders (such as major depression, bipolar depression, and dysthymic disorder), sleep disorders (narcolepsy), obesity, tinnitus, stroke, traumatic brain injury, Alzheimer's, and anorexia.

The physiologic signals that are selected, stored and reported in accordance with various aspects of the invention may include any number of sensed signals. Such physiological signals can include, for example, electrical signals (such as EEG, ECoG and/or EKG), chemical signals, biological signals (such as change in quantity of neurotransmitters), temperature signals, pressure signals (such as blood pressure, intracranial pressure or cardiac pressure), respiration signals, heart rate signals, pH-level signals, activity signals (e.g., detected by an accelerometer), and/or peripheral nerve signals (cuff electrodes on a peripheral nerve). Such physiological signals may be recorded using one or more monitoring elements such as monitoring electrodes or sensors. For example, U.S. Pat. No. 6,227,203 provides examples of various types of sensors that may be used to detect a symptom or a condition or a nervous system disorder and responsively generate a neurological signal. In addition, various types of physiologic activities may be sensing including, for example, brain, heart and/or respiration.

As discussed, the techniques disclosed herein are suitable for use within any implantable medical device system including, but not limited to, a core monitoring device, a full monitoring device, and/or a combination monitoring and treatment device. Each of these medical device implementations are discussed in further detail below. In general, however, each of these embodiments utilize one or more monitoring elements that receive signals associated with the physiological conditions being sensed, a memory component that contains multiple data structures (for example, at least one that is age-based and at least one other that is priority-based), and a processing component (logic or software) that stores data records in the data structures as disclosed herein (utilizing, for example, severity and priority determinations for the data).

Core Monitor

In an embodiment, a Core Monitor device monitors cardiac (ECG) and respiration signals and records these signals as discussed herein. Real-time analysis of the ECG signal evaluates rate disturbances (e.g., bradycardia; tachycardia; asystole) as well as any indications of cardiac ischemia (e.g., ST segment changes; T wave inversion, etc.). Real-time analysis of the respiration signal evaluates respiration disturbances (e.g., respiration rate, minute ventilation, apnea, prolonged pauses, etc.). Abnormalities detected during real-time analysis may lead to an immediate patient alert, which can be audible (beeps, buzzers, tones, spoken voice, etc.), light, tactile, or other means. Manual indication of a seizure may be achieved through an external activator device 22. The patient (or caregiver) may push a button on the external device, while communicating with the implanted device. This will provide a marker and will initiate a recording, as discussed herein, of the sensed data (for example, in the event the patient is experiencing a neurological event).

In treating SUDEP, for example, prolonged ECG recordings may be possible (e.g., recording all data during sleep since the incidence of SUDEP is highest in patients during sleep). Post-processing of the signal can occur in the implanted device, the patient's external device and/or in the clinician external device. Intermittently (e.g., every morning, once/week, following a seizure), the patient may download data from the implantable device to the patient external device (as will be discussed further herein), which may then be analyzed by the external device (and/or sent through a network to the physician) to assess any ECG abnormalities. If an abnormality is detected, the device may notify the patient/caregiver. At that time, the patient/caregiver may inform the healthcare provider of the alert to allow a full assessment of the abnormality. The clinician external device may also be capable of obtaining the data from the implanted device and conducting an analysis of the stored signals. If a potentially life-threatening abnormality is detected, the appropriate medical treatment may be prescribed (e.g., cardiac abnormality: a pacemaker, an implantable defibrillator, or a heart resynchronization device may be indicated or respiration abnormality: CPAP, patient positioning, or stimulation of respiration may be indicated).

FIG. 1 is a simplified schematic view of a core monitor 100 implanted in a patient 10, monitor 100 continuously senses and monitors one or more physiological conditions of the patient via monitoring elements 140 (in the embodiment, the physiological conditions are cardiac and respiration functions of patient 10 and the monitoring elements 140 are subcutaneous electrodes). Stored diagnostic data is uplinked and evaluated by an external computing device 120 (e.g., a patient's physician utilizing programmer) via a 2-way telemetry link 132. An external patient activator 122 may optionally allow the patient 110, or other care provider (not shown), to manually activate the recording of diagnostic data.

In the embodiment, monitor 100 encompasses monitoring elements 140 that are several subcutaneous spiral electrodes and may be embedded individually into three or four recessed casings placed in a compliant surround that is attached to the perimeter of implanted monitor 100 as substantially described in U.S. Pat. Nos. 6,512,940 and 6,522,915. These electrodes are electrically connected to the circuitry of the implanted monitor 100 to allow the detection of cardiac depolarization waveforms (as substantially described in U.S. Pat. No. 6,505,067) that may be further processed to detect cardiac electrical characteristics (e.g., heart rate, heart rate variability, arrhythmias, cardiac arrest, sinus arrest and sinus tachycardia). Further processing of the cardiac signals signal amplitudes may be used to detect respiration characteristics (e.g., respiration rate, minute ventilation, and apnea). To aid in the implantation of monitor 100 in a proper position and orientation, an implant aid may be used to allow the implanting physician to determine the proper location/orientation as substantially described in U.S. Pat. No. 6,496,715.

Figure 2:
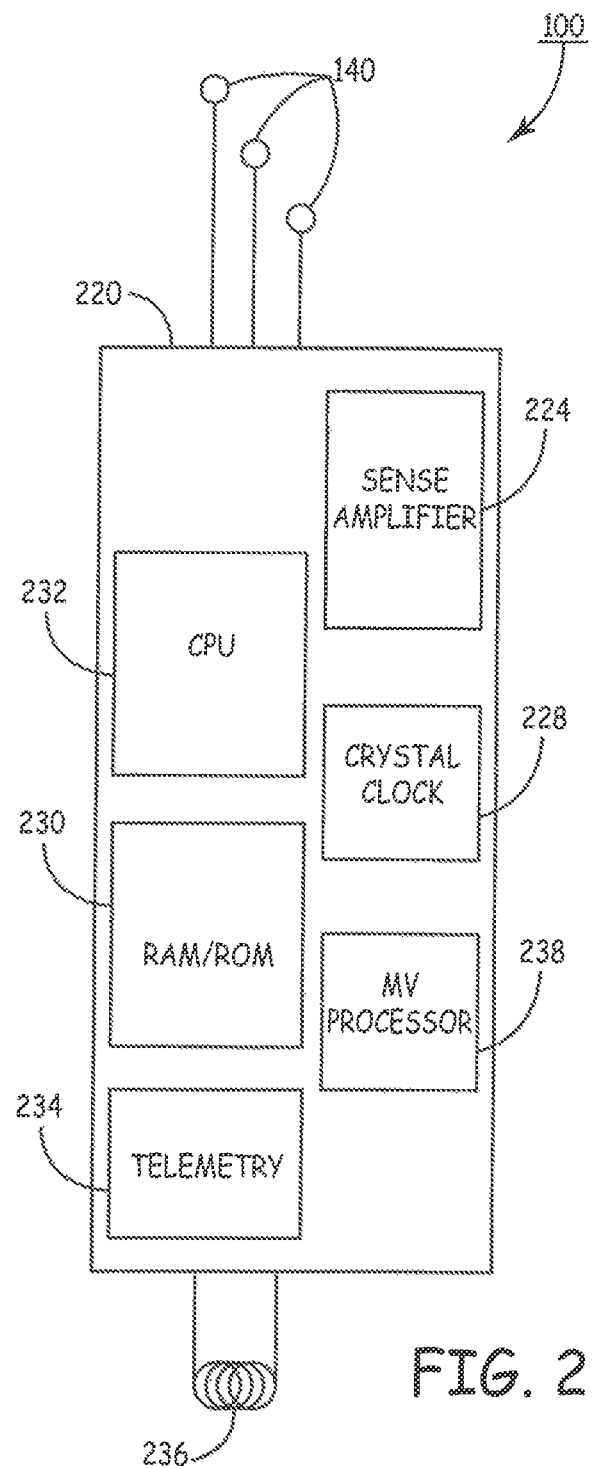
FIG. 2 is a simplified block diagram of a core monitor as shown in FIG. 1.

FIG. 2 depicts a block diagram of the electronic circuitry of the core monitor 100 of FIG. 1 in accordance with an embodiment of the invention. Monitor 100 comprises a primary control circuit 220 and may be similar in design to that disclosed in U.S. Pat. No. 5,052,388. Primary control circuit 220 includes sense amplifier circuitry 224, a crystal clock 228, a random-access memory and read-only memory (RAM/ROM) unit 230, a central processing unit (CPU) 232, a MV Processor circuit 238 and a telemetry circuit 234, all of which are generally known in the art.

Monitor 100 may include internal telemetry circuit 234 so that it is capable of being programmed by means of external programmer/control unit 120 via a 2-way telemetry link 132 (shown in FIG. 1). External programmer/control unit 120 communicates via telemetry with the monitor 100 so that the programmer can transmit control commands and operational parameter values to be received by the implanted device, and so that the implanted device can communicate diagnostic and operational data to the programmer 120. For example, programmer 120 may be Models 9790 and CareLink® programmers, commercially available from Medtronic, Inc., Minneapolis, Minn. Various telemetry systems for providing the necessary communications channels between an external programming unit and an implanted device have been developed and are well known in the art. Suitable telemetry systems are disclosed, for example, in U.S. Pat. Nos. 5,127,404; 4,374,382; and 4,556,063.

Typically, telemetry systems such as those described in the above referenced patents are employed in conjunction with an external programming/processing unit. Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modeled as an air-core coupled transformer. An example of such a telemetry system is shown in U.S. Pat. No. 4,556,063.

In order to communicate digital data using RF telemetry, a digital encoding scheme such as is described in U.S. Pat. No. 5,127,404 can be used. In particular, a pulse interval modulation scheme may be employed for downlink telemetry, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encode a digital "0" bit while a longer interval encodes a digital "1" bit. For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen-position data frame may be defined, wherein a pulse in one of the time slots represents a unique four-bit portion of data.

Programming units such as the above-referenced Medtronic Models 9790 and CareLink® programmers typically interface with the implanted device through the use of a programming head or programming paddle, a handheld unit adapted to be placed on the patients body over the implant site of the patients implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

As previously noted, primary control circuit 220 includes central processing unit 232 which may be an off-the-shelf programmable microprocessor or microcontroller, but in an embodiment of the invention is a custom integrated circuit. Although specific connections between CPU 232 and other components of primary control circuit 220 are not shown in FIG. 2, it will be apparent to those of ordinary skill in the art that CPU 232 functions to control the timed operation of sense amplifier circuit 224 under control of programming stored in RAM/ROM unit 230. Those of ordinary skill in the art will be familiar with such an operative arrangement.

With continued reference to FIG. 2, crystal oscillator circuit 228, in an embodiment, is a 32,768-Hz crystal controlled oscillator, provides main timing clock signals to primary control circuit 220. The various components of monitor 100 are powered by means of a battery (not shown), which is contained within the hermetic enclosure of monitor 100. For the sake of clarity in the figures, the battery and the connections between it and the other components of monitor 100 are not shown. Sense amplifier 224 is coupled to monitoring elements 140. Where cardiac intrinsic signals are sensed, they may sensed by sense amplifier 224 as substantially described in U.S. Pat. No. 6,505,067.

Processing by CPU 232 allows the detection of cardiac electrical characteristics and anomalies (e.g., heart rate, heart rate variability, arrhythmias, cardiac arrest, sinus arrest and sinus tachycardia). Further processing of the cardiac signals signal amplitudes may be used to detect respiration characteristics/anomalies (e.g., respiration rate, tidal volume, minute ventilation, and apnea) in MV Processor 238.

Figure 3:
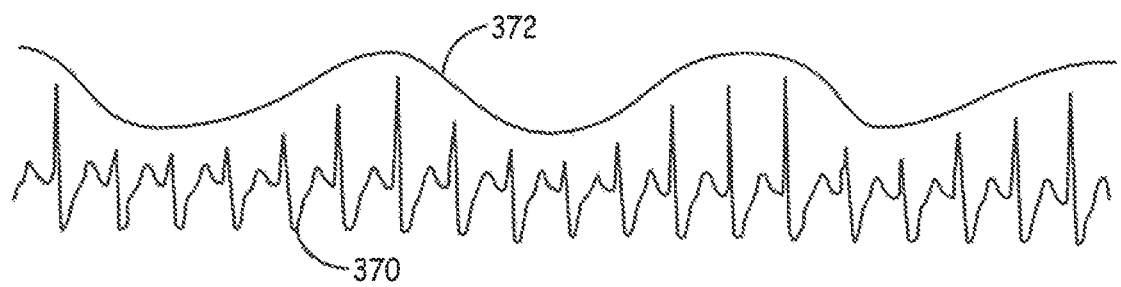
FIG. 3 is a graphical representation of the signals sensed by core monitor as shown in FIG. 1 above.

FIG. 3 shows the intracardiac signals 370 presented to sense amplifier 224 from monitoring elements 140. Note the amplitude variation of cardiac signals caused by the change in thoracic cavity pressure due to respiration (i.e., inspiration and expiration). By low pass filtering the cardiac signals 370, a signal representing minute ventilation may be obtained as depicted in waveform 372. This respiration signal may further be examined to detect respiration rate and reduced or absence of inspiration and expiration (central apnea) by CPU 232 and software resident in RAM/ROM 230.

Upon detection of either a cardiac or respiration anomaly, CPU 232, under control of firmware resident in RAM/ROM 230, will initiate recording of the appropriate diagnostic information into RAM of RAM/ROM 230 (discussed further herein), initiate a warning or alert to the patient, patient caregiver, or remote monitoring location.

Figure 4:
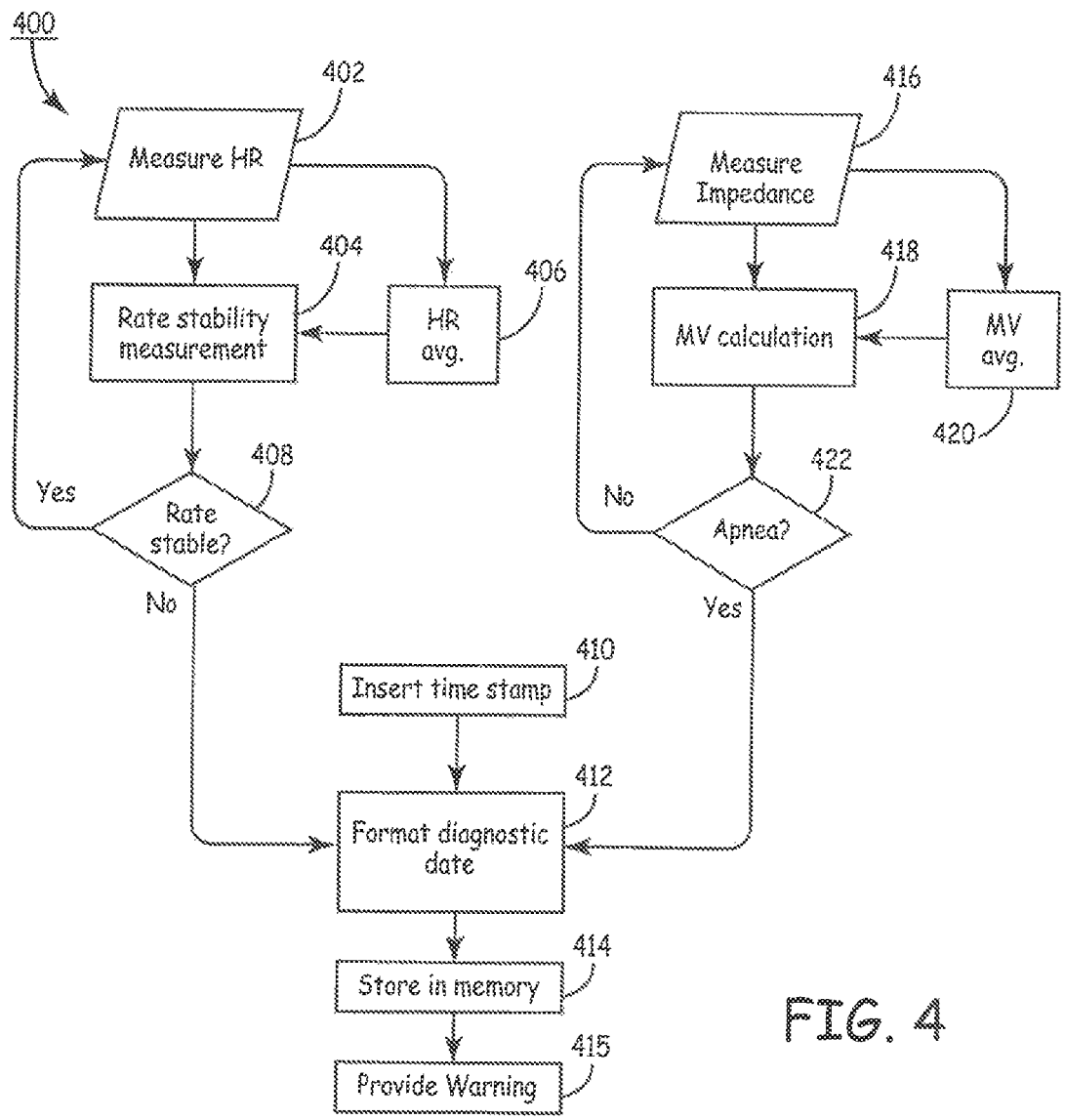
FIG. 4 is a flow diagram showing operation of a core monitor as shown in FIG. 1 above.

FIG. 4 is a flow diagram 400 showing operation of a core monitor sensing/monitoring cardiac and respiration parameters for the detection of a neurological event as shown and described in FIG. 1 above. Beginning at block 402, the interval between sensed cardiac signals are measured. At block 404, a rate stability measurement is made on each cardiac interval utilizing a heart rate average from block 406. At block 408, a rate stable decision is made based upon preprogrammed parameters. If YES, the flow diagram returns to the HR Measurement block 402. If NO, the rate stability information is provided to Format Diagnostic Data block 412.

At block 416, thoracic impedance is continuously measured in a sampling operation. At block 418, a MV and respiration rate calculation is made. At block 420, a MV average calculation may be made and inputted to block 418. At block 422, a pulmonary apnea decision is made based upon preprogrammed criteria. If NO, the flow diagram returns to MV Measurement block 416. If YES, the occurrence of apnea and MV information is provided to Format Diagnostic Data block 412. Format Diagnostic Data block 412 formats the data from the cardiac and respiration monitoring channels, adds a time stamp (i.e., date and time) and provides the data to block 414 where the data is stored in RAM, SRAM or MRAM memory for later retrieval by a clinician via telemetry (using the techniques discussed herein). Optionally, block 412 may add examples of intrinsic ECG and/or respiration signals recorded during a sensed neurological event. Additionally, optionally, block 415 may initiate a warning or alert to the patient, patient caregiver, or remote monitoring location (as described in U.S. Pat. No. 5,752,976).

It will be appreciated that alternative embodiments of the core monitor device may also be utilized. As discussed above, core monitor 100 may sense any number of physiologic conditions of the patient for purposes of detecting, and storing data relating to, any number of the neurological events. For example, cardiac lead(s) may be used to facilitate detection of a neurological event and the recording of data and signals pre and post event. Cardiac leads may consist of any typical lead configuration as is known in the art, such as, without limitation, right ventricular (RV) pacing or defibrillation leads, right atrial (RA) pacing or defibrillation leads, single pass RA/RV pacing or defibrillation leads, coronary sinus (CS) pacing or defibrillation leads, left ventricular pacing or defibrillation leads, pacing or defibrillation epicardial leads, subcutaneous defibrillation leads, unipolar or bipolar lead configurations, or any combinations of the above lead systems.

In another embodiment, an electrode located distally on a sensor stub may be used to facilitate detection of a neurological event and the recording of data and signals pre and post event. The sensor stub is inserted subcutaneously in a thoracic area of the patient. The monitor 100 may sense cardiac signals between an electrode on the distal end of the sensor stub and the monitor case as described in conjunction with the embodiment shown in FIG. 5 in U.S. Pat. No. 5,987,352. The monitor 100 may also sense respiration parameters such as respiration rate, minute ventilation and apnea via measuring and analyzing the impedance variations measured from the implanted monitor 100 case to the electrode located distally on the sensor stub lead as substantially described in U.S. Pat. Nos. 4,567,892 and 4,596,251.

In yet another embodiment, an external wearable device such as a wearable patch, a wristwatch, or a wearable computing device may be used may be used to continuously sense and monitor cardiac and respiration function of patient 10. Optionally, a button on the external wearable device may be activated by the patient 10 (or a caregiver) to manually activate data recording (for example, in the event the patient is experiencing a neurological event). The external wearable device may comprise an amplifier, memory, microprocessor, receiver, transmitter and other electronic components as substantially described in U.S. Pat. No. 6,200,265. In the embodiment of a wearable patch, the device may consist of a resilient substrate affixed to the patient's skin with the use of an adhesive. The substrate flexes in a complimentary manner in response to a patient's body movements providing patient comfort and wearability. The low profile patch is preferably similar in size and shape to a standard bandage, and may be attached to the patient's skin in an inconspicuous location.

Figure 5:
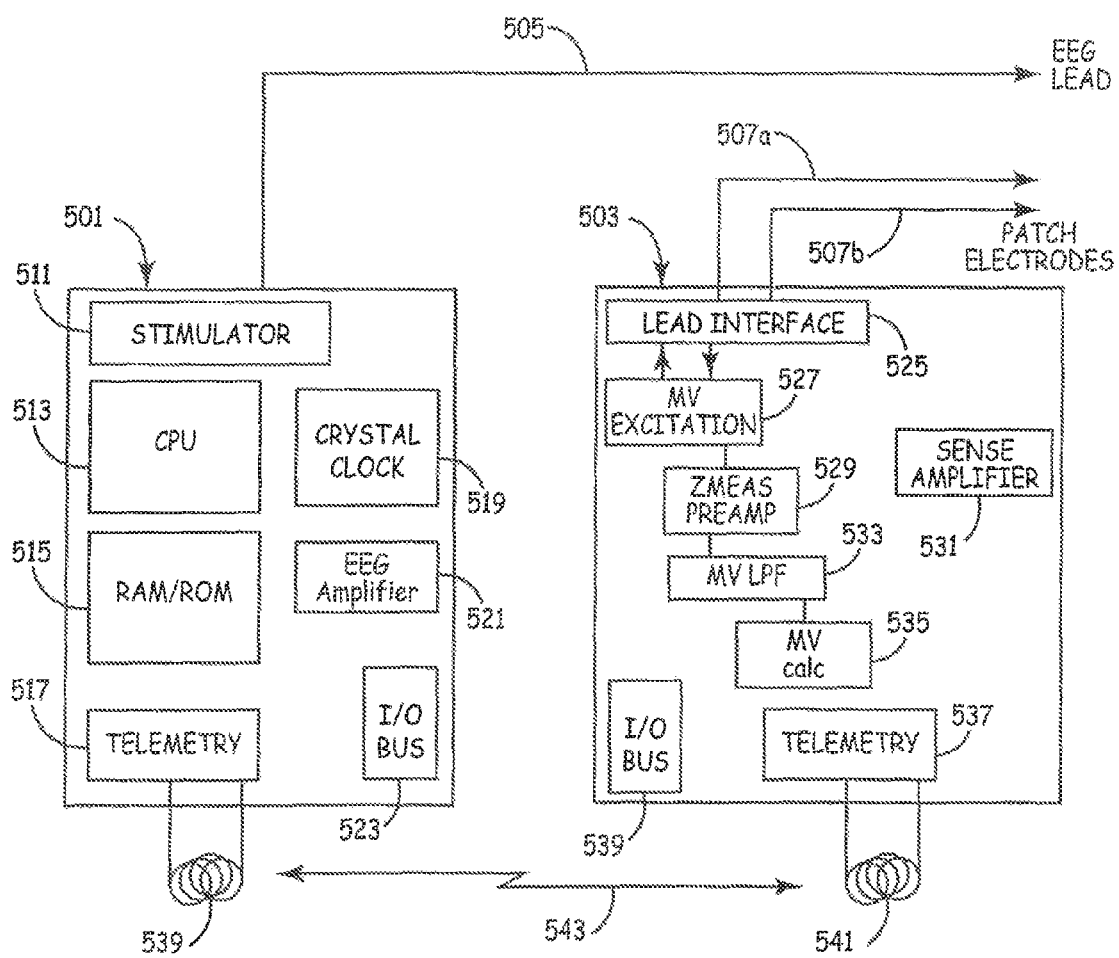
FIG. 5 shows a first apparatus for collecting physiologic data that can be retained in accordance with an embodiment of the invention.

FIG. 5 shows an apparatus 500 for collecting physiologic data that can be retained in accordance with an embodiment of the invention. Apparatus comprises implanted device 501 and external device 503. In the embodiment, implanted device 501 collects physiological data through EEG lead 505, which is coupled to an electrode. The embodiment may support a plurality of electrodes that may collect physiological data from desired locations in the brain or other neural tissue within the body. With respect to sensing of the brain, the embodiment may support electrodes that are positioned in the brain, positioned on the scalp, or a combination. EEG amplifier 521 processes neurological signals from EEG lead 505, while stimulator 511 forms appropriate electrical waveforms to simulate electrodes that are coupled to EEG lead 505. CPU 513 controls the circuitry in internal device 501 and is clocked by crystal clock 519. CPU 513 obtains instructions from and stores neurological data to RAM/ROM 515. Communication within internal device between components is transported on I/O bus 523.

External device 503 collects other physiologic data through patch leads 507a and 507b, which are coupled to patch electrodes. External device 503 is typically worn by the patient. In the embodiment, the patch electrodes monitor and stimulate the respiration of the patient in concert with monitoring neurological data. Respiratory data is collected from the patch electrodes through lead interface 525. Minute Ventilation (MV) module 527 excites the patch electrodes (if necessary) while respiratory data (indicative of the minute ventilation) is obtained through sense amplifier 531. (Minute or total ventilation is the product of respiratory rate and tidal volume.) Additionally, impedance module 529, MV low pass filter 533, and MV calibration module 535 calibrate MV excitation module 527. Data communication within external device 503 is transported on I/O bus 539.

Internal device 501 and external device 503 communicate with each other over telemetry channel 543 through telemetry interfaces 517 and 537 and antennas 539 and 541. However, internal device 501 and external device 503 may communicate using an alternative communications path. For example, I/O bus 523 and I/O bus 539 may be electrically connected through a wired channel.

While the embodiment shown in FIG. 5 collects and retains physiological data and respiratory data, other physiologic data may be collected and retained. For example, apparatus 500 may collect cardiac data and motor coordination data. The embodiment may further correlate the neurological data with the physiological data.

Full Monitor

The full monitor is capable of monitoring cardiopulmonary parameters as in the core monitor described above, and additionally an EEG from an intracranially implanted lead system. This will allow the full monitor to collect cardiovascular, respiratory and neurologic signals in close proximity to detected neurologic events as well as notifying the patient/caregiver of a prolonged event (and/or status epilepticus). Like the core monitor, cardiovascular and respiratory monitoring may occur around a neurologic event (peri-ictal). The full monitor device may detect the neurological event and analyze the peri-ictal signals and initiate loop recording. The addition of the neurologic monitor allows shorter loop-recording durations since the beginning of the neurological event may be known with greater certainty. In addition, the EEG monitoring may be programmed to provide alerts when a neurologic event has exceeded a pre-determined duration or severity.

Figure 6:
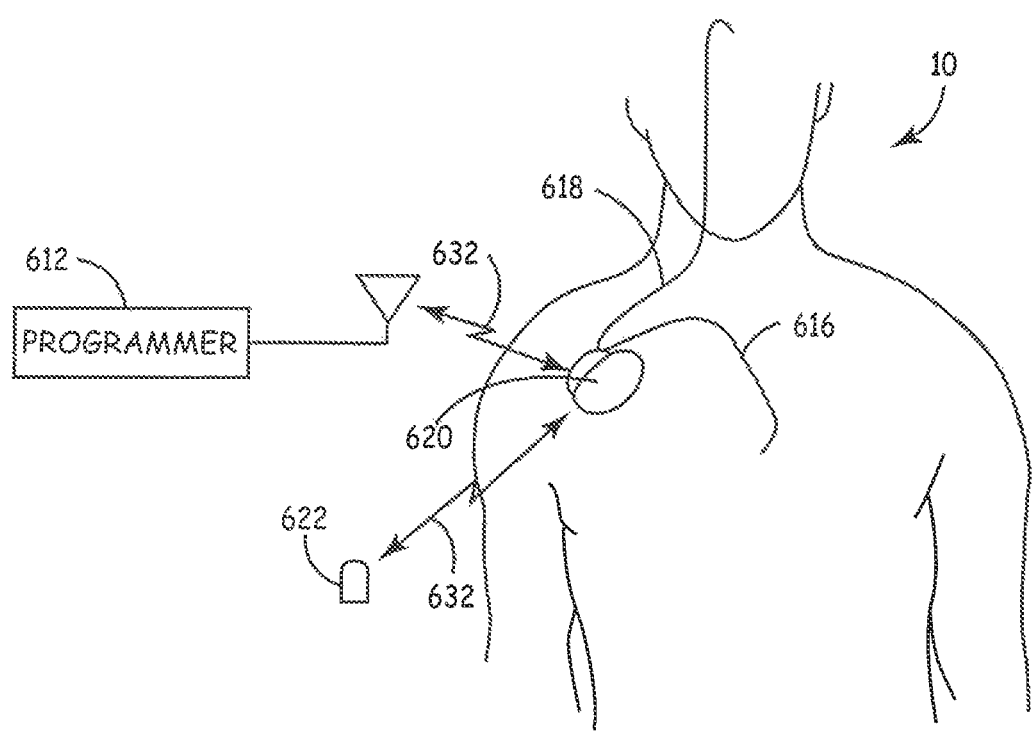
FIG. 6 is a simplified schematic view of an alternative embodiment of a thoracic and cranial leaded medical device implanted in a patient that monitors cardiac, respiratory and brain parameters in accordance with an embodiment of the invention.

FIG. 6 is a simplified schematic view of a full monitor 620 implanted in a patient 10. Monitor 620 continuously senses and monitors cardiac, brain and respiration function of patient 10 via several subcutaneous electrodes 616 and a brain lead 618 to allow detection of neurological events and the recording of data and signals pre and post event. Stored diagnostic data is uplinked and evaluated by the patient's physician utilizing programmer 612 via a 2-way telemetry link 632. An external patient activator 622 may optionally allow the patient 10, or other care provider (not shown), to manually activate the recording of diagnostic data. An implant aid may be used with monitor 620 to ensure a proper position and orientation during implant as described above in connection with the system of FIG. 1.

Figure 7:
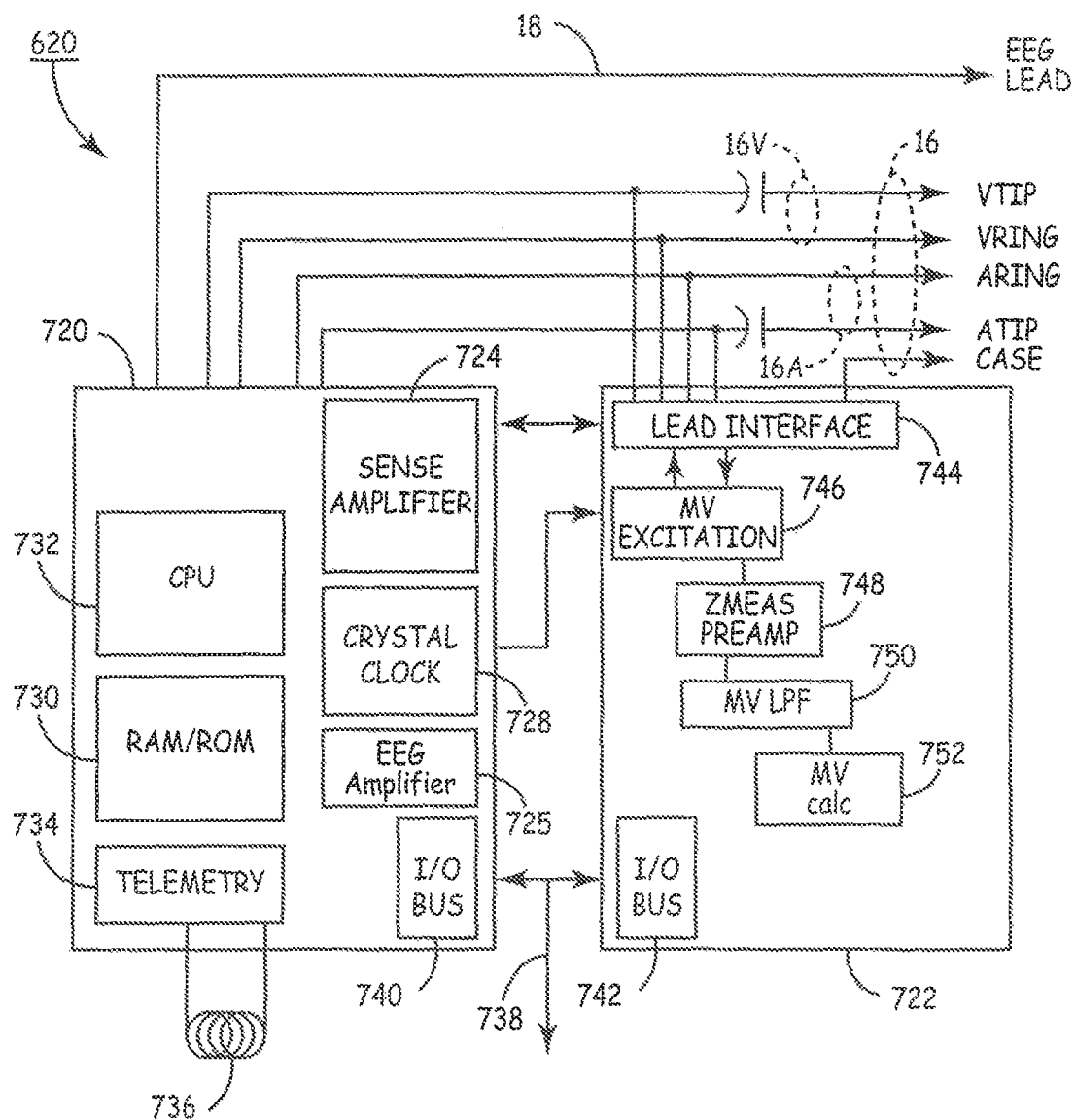
FIG. 7 is a simplified block diagram of a full monitor as shown in FIG. 6 above.

FIG. 7 is a block diagram of the electronic circuitry that makes up full monitor 620 with brain lead 618 and cardiac 616 leads 616 (which includes leads 616A and 616V) of FIG. 6 in accordance with the disclosed alternative embodiment of the invention. Cardiac leads 616V represent the grouping of VTIP and VRING. Cardiac leads 616A represent the grouping of ATIP and ARING. Monitor 620 comprises a primary control circuit 720 and MV circuit 722 that are described herein above in conjunction with FIG. 2. In addition, the full Monitor 620 also includes an amplifier 725 to amplify and sense EEG signals from a cranially implanted lead 618. The CPU 732, in conjunction with a software program resident in RAM/ROM 730, integrates the information from the sensed cardiac, respiration and EEG signals, detects the onset of cerebral, cardiac and/or respiratory anomalies, formats and stores diagnostic data for later retrieval by the patient's clinician and, optionally, may warn or alert the patient, patient caregiver or remote monitoring location. Sense amplifier circuit 724 is like sense amplifier circuit 224 in FIG. 2. Crystal clock 728 is like crystal clock 519 in FIG. 5. Telemetry interface 734 is like telemetry interface 517 in FIG. 5. Antenna 736 is like antenna 519 in FIG. 5. I/O bus 740 is like I/O bus 523 in FIG. 5. I/O bus 742 is like I/O bus 539 in FIG. 5. MV calibration module 752 is like MV calibration module 535 in FIG. 5. MV low pass filter 750 is like MV low pass filter 533 in FIG. 5. Impedance module 748 is like impedance module 529 in FIG. 5. MV excitation module 746 is like MV excitation module 527 in FIG. 5. Lead interface 744 is like lead interface 525 in FIG. 5. Communication link 738 connects additional I/O buses or other devices.

Figure 8:
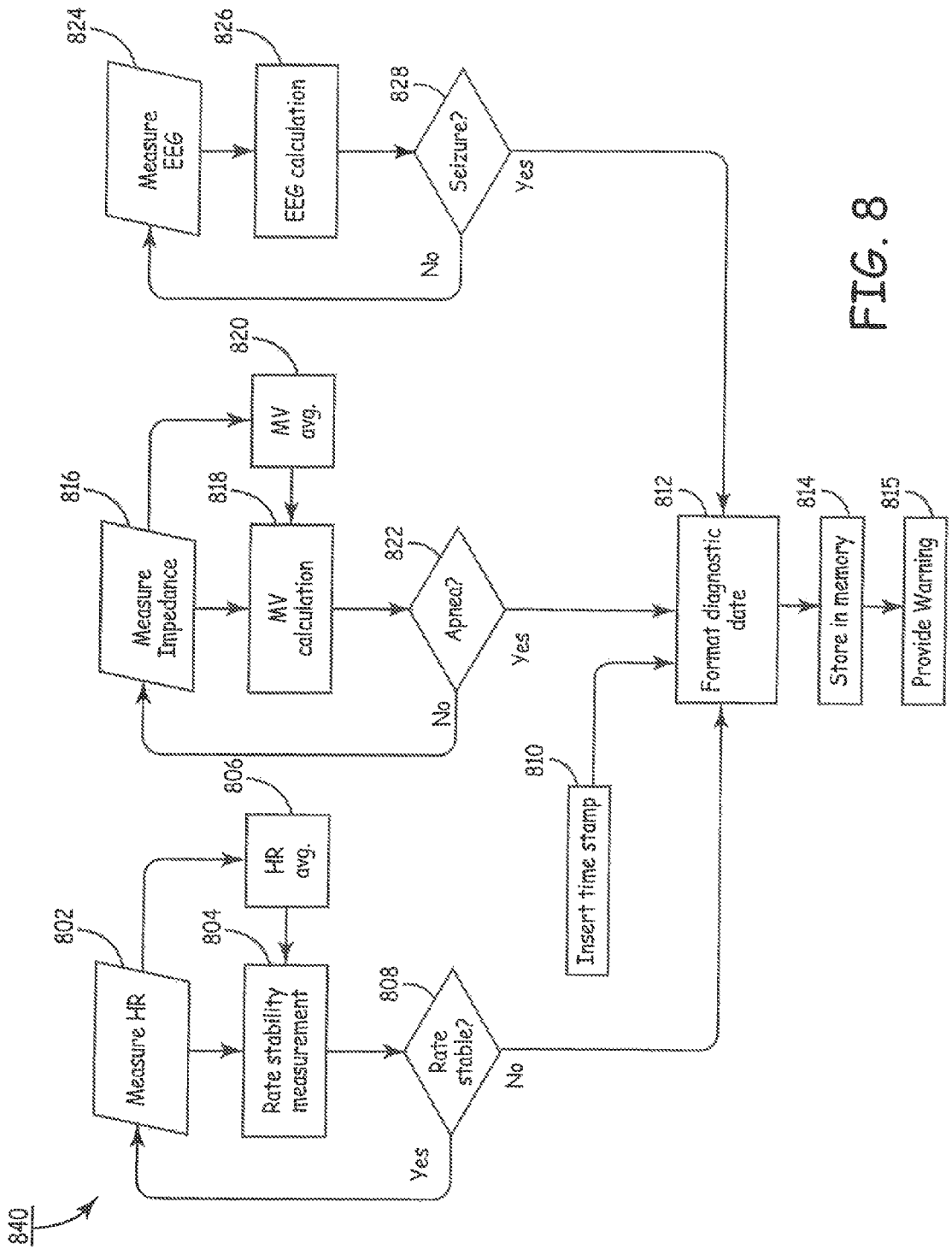
FIG. 8 is a flow diagram showing operation of a full monitor as shown in FIG. 6 above.

FIG. 8 is a flow diagram 840 showing operation of a full monitor sensing and monitoring cardiac, respiration and electroencephalogram parameters for the detection of a neurological event as shown and described in embodiment in FIG. 6 above. Beginning at block 802, the interval between sensed cardiac signals are measured. At block 804, a rate stability measurement is made on each cardiac interval utilizing a heart rate average from block 806. At block 808, a rate stable decision is made based upon preprogrammed parameters. If YES, the flow diagram returns to the HR Measurement block 802. If NO, the rate stability information is provided to Format Diagnostic Data block 812.

At block 816, thoracic impedance is continuously measured in a sampling operation. At block 818, a MV and respiration rate calculation is made. At block 822, a pulmonary apnea decision is made based upon preprogrammed criteria. If NO, the flow diagram returns to MV Measurement block 816. If YES, the occurrence of apnea and MV information is provided to Format Diagnostic Data block 812.

At block 824, the electroencephalogram is sensed and measured. An EEG seizure determination is performed at block 826 as described in U.S. Patent Application Publication No. 2004/0138536. At block 828, a seizure cluster episode is determined. If NO, the flow diagram returns to EEG Measurement block 824. If YES, the occurrence of a seizure cluster is provided to Format Diagnostic Data block 812. Format Diagnostic Data block 812 formats the data from the cardiac, respiration and EEG monitoring channels, adds a time stamp (i.e., date and time) and provides the data to block 814 where the data is stored in RAM memory for later retrieval by a clinician via telemetry (using techniques discussed herein). Optionally, block 812 may add examples of intrinsic ECG, respiration and/or EEG signals recorded during a sensed episode/seizure. Additionally, optionally, block 815 may initiate a warning or alert to the patient, patient caregiver, or remote monitoring location (as described in U.S. Pat. No. 5,752,976).

Again, it will be appreciated that alternative embodiments of the lull monitor device may also be utilized. For example, cardiac lead(s), a sensor stub, and/or a wearable patch may be used to facilitate detection of a neurologic event and the recording of data and signals pre and post event. An integrated electrode may also be used that senses ECG signals as described in U.S. Pat. No. 5,987,352 and respiration signals as described in U.S. Pat. Nos. 4,567,892 and 4,596,251. Optionally, the monitor may warn/alert the patient 10 via buzzes, tones, beeps or spoken voice (as substantially described in U.S. Pat. No. 6,067,473) via a piezo-electric transducer incorporated in the housing of monitor and transmitting sound to the patient's inner ear.

In another embodiment, the monitor may be implanted cranially in the patient 10. In such an embodiment, the monitor may be constructed as substantially described in U.S. Pat. Nos. 5,782,891 and 6,427,086. EEG sensing may be accomplished by the use of integrated electrodes in the housing of the monitor, cranially implanted leads, and or leadless EEG sensing.

Alternatively, ECG rate and asystole may be inferred using a variety of technologies. For example, ECG rate and asystole may be inferred (along with a blood pressure signal) from a capacitive dynamic pressure signal dP/dt as substantially described in U.S. Pat. No. 4,485,813. Similarly, an acoustic signal (i.e., sound) may be used as substantially described in U.S. Pat. No. 5,554,177 (the sensed acoustic signal is low pass filtered to limit ECG signals to 0.5-3 Hz while filtering out speech, swallowing and chewing sounds). As another example, ECG rate and asystole may be inferred (along with a blood saturation measurement) by monitoring a reflectance oximetry signal (i.e., $O_2$sat) as substantially described in U.S. Pat. No. 4,903,701. As yet another example, a blood temperature signal (i.e., dT/dt) may be used as substantially described in U.S. Pat. No. 5,336,244. As still another example, ECG rate and asystole may be inferred (along with an arterial flow measurement) by monitoring a blood flow signal (from an adjacent vein via impedance plethysmography, piezoelectric sensor or Doppler ultrasound) as substantially described in U.S. Pat. No. 5,409,009. As another example, ECG rate and asystole may be inferred (along with a blood pressure measurement) by monitoring a blood pressure signal utilizing a strain gauge s substantially described in U.S. Pat. No. 5,168,759. As another example, ECG rate and asystole may be inferred by monitoring a blood parameter sensor (such as oxygen, pulse or flow) located on a V-shaped lead as substantially described in U.S. Pat. No. 5,354,318.

Monitor and Treat

As exemplified above, any number of implantable medical device systems are envisioned that may incorporate the recording and retention techniques discussed herein. For example, the monitoring may be achieved using any of the above techniques in conjunction with treatment by delivery of treatment therapy (e.g., electrical stimulation) to the brain, cardiac or respiration.

Figure 9:
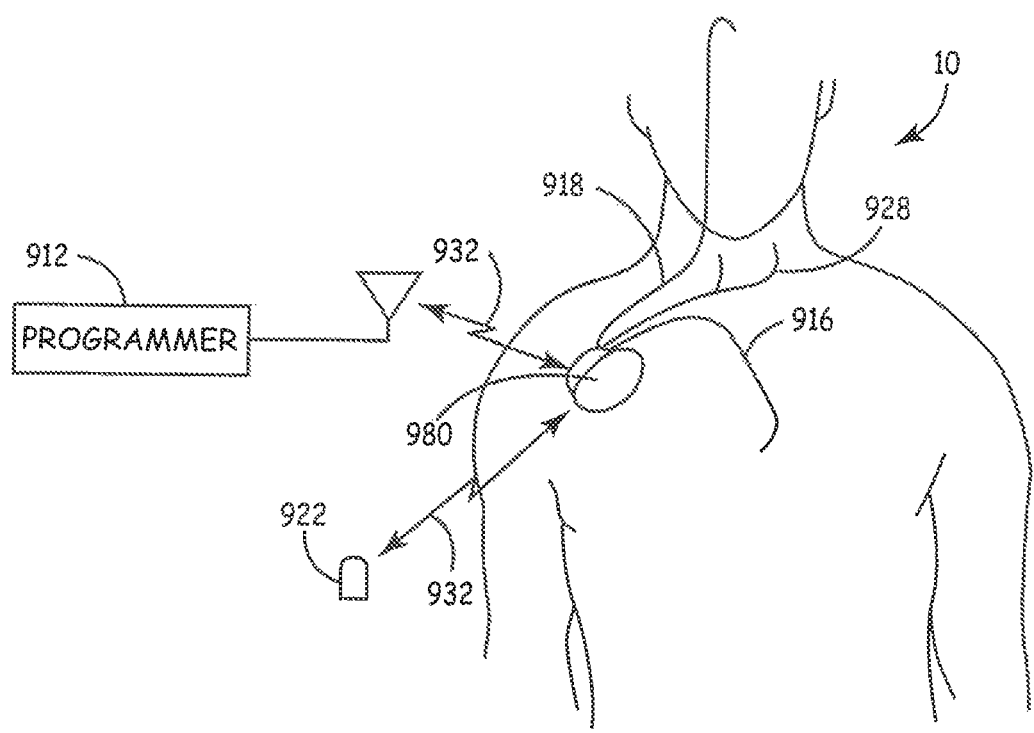
FIG. 9 is a simplified schematic view of another embodiment of a cardiac, cranial and phrenic nerve leaded medical device implanted in a patient that monitors cardiac, respiratory and brain parameters and provides brain, respiration, and cardiac treatment thereof in accordance with an embodiment of the invention.

FIG. 9 is a simplified schematic view of a full Monitor/Brain, Respiration and Cardiac Therapy unit 980 implanted in a patient 10. Monitor/Brain, Respiration and Cardiac Therapy unit 980 continuously senses and monitors cardiac, brain and/or respiration function of patient 10 via cardiac lead(s) 916 and a brain lead 918 to allow detection of epileptic neurological events, the recording of data and signals pre and post event, and the delivery of therapy via brain lead 918, cardiac lead(s) 916 and phrenic nerve lead 928. Stored diagnostic data is uplinked and evaluated by the patient's physician utilizing programmer 912 via a 2-way telemetry link 932. An external patient activator 922 may optionally allow the patient 10, or other care provider (not shown), to manually activate the recording of diagnostic data and delivery of therapy. Optionally, lead 928 may connect to the diaphragm to provide direct diaphragmatic stimulation. As discussed any combination of monitoring and any combination of treatment may be implemented.

Figure 10:
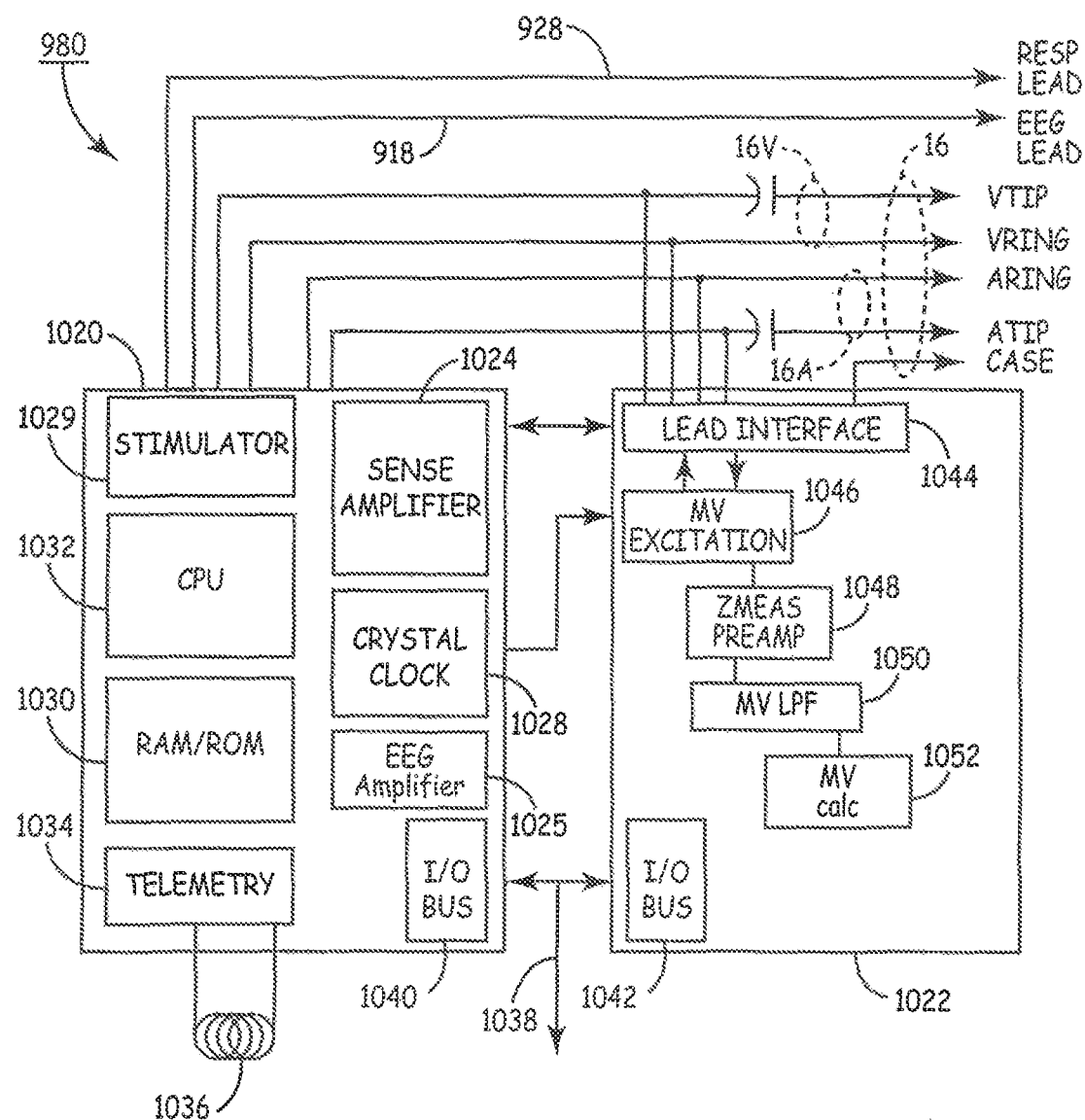
FIG. 10 is a simplified block diagram of a full monitor with brain, respiration and cardiac stimulation therapy as shown in FIG. 9 above.

FIG. 10 is a block diagram of the electronic circuitry that makes up full Monitor/Brain, Respiration and Cardiac Therapy device 980 of FIG. 9. Monitor/Brain, Respiration and Cardiac Therapy device 980 comprises a primary control circuit 1020 and MV circuit 1022 whose function was described herein above in conjunction with FIG. 2. In addition the Monitor/Brain, Respiration and Cardiac Therapy device of FIG. 10 also includes an amplifier 1025 to amplify and sense EEC signals from a cranially implanted lead 918 and an output stimulator 1029 to provide brain stimulation via cranially implanted lead 918 and phrenic nerve stimulation via respiration lead 928. The CPU 1032, in conjunction with software program in RAM/ROM 1030, integrates the information from the sensed cardiac, respiration and EEG signals, detects the onset of cerebral, cardiac and/or respiratory anomalies, provides preprogrammed stimulation therapy to the patient's brain via lead 918, stimulation of the patient's phrenic nerve via respiration lead 928 and stimulation of the patient's heart via cardiac leads 916 (which includes leads 916A and 916V), formats and stores diagnostic data for later retrieval by the patient's clinician and, optionally, may warn or alert the patient, patient caregiver or remote monitoring location. Cardiac leads 916V represent the grouping of VTIP and VRING. Cardiac leads 916A represent the grouping of ATP and ARING. Optionally, lead 928 may connect to the diaphragm to provide direct diaphragmatic stimulation. Sense amplifier circuit 1024 is like sense amplifier circuit 224 in FIG. 2. Crystal clock 1028 is like crystal clock 519 in FIG. 5. Telemetry interface 1034 is like telemetry interface 517 in FIG. 5. Antenna 1036 is like antenna 519 in FIG. 5. I/O bus 1040 is like I/O bus 523 in FIG. 5 I/O bus 1042 is like I/O bus 539 in FIG. 5. MV calibration module 1052 is like MV calibration module 535 in FIG. 5. MV low pass filter 1050 is like MV low pass filter 533 in FIG. 5. Impedance module 1048 is like impedance module 529 in FIG. 5. MV excitation module 1046 is like MV excitation module 527 in FIG. 5. Lead interface 1044 is like lead interface 525 in FIG. 5. Communication link 1038 connects additional I/O buses or other devices.

Figure 11:
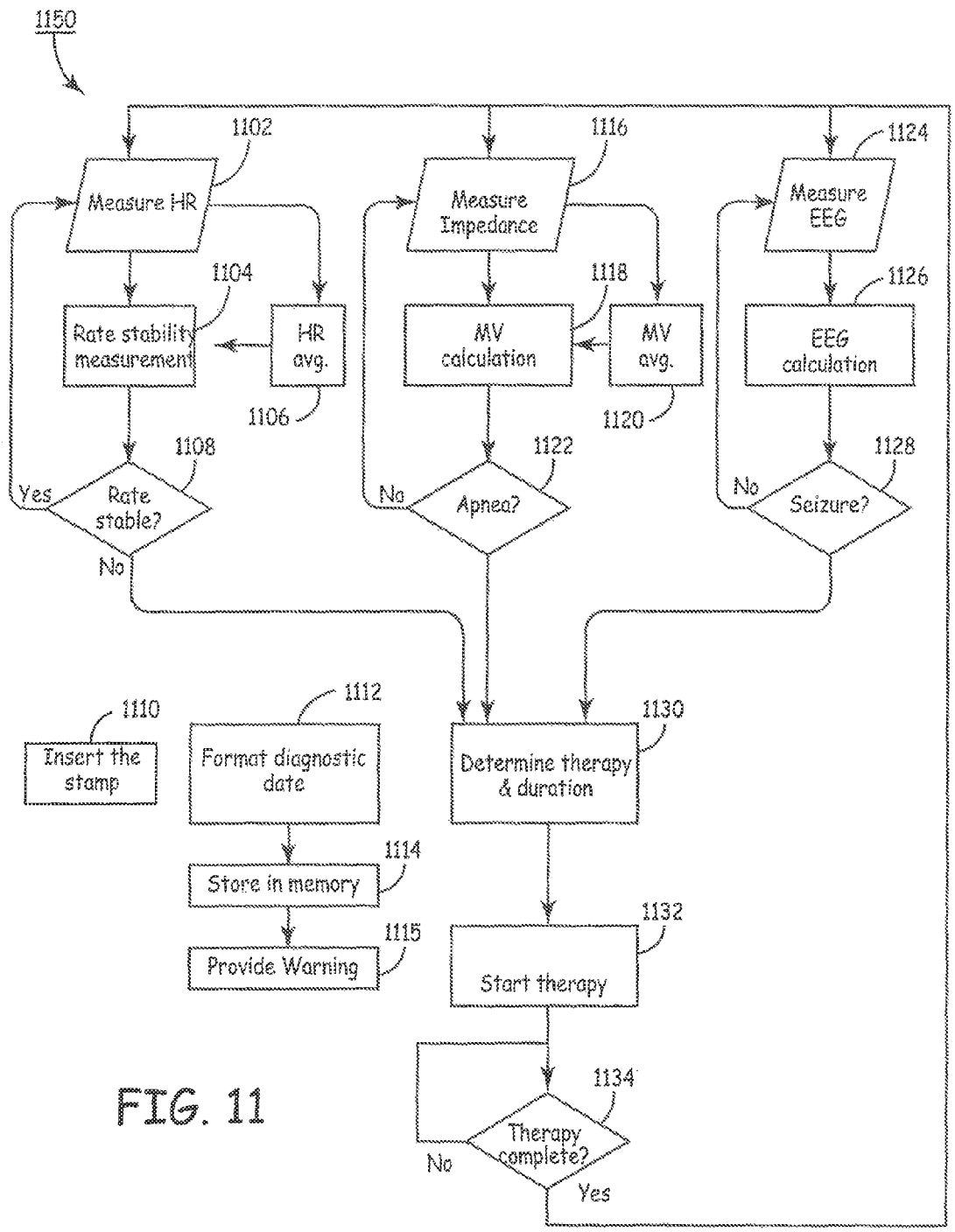
FIG. 11 is a flow diagram showing operation of a full monitor with therapy (including brain, respiration and/or cardiac stimulation therapy) as shown in FIG. 9 above.

FIG. 11 is a flow diagram 1150 showing operation of a full monitor/therapy sensing and monitoring cardiac, respiration and electroencephalogram parameters as shown and described in FIG. 9 above. Beginning at block 1102, the interval between sensed cardiac signals are measured. At block 1104, a rate stability measurement is made on each cardiac interval utilizing a heart rate average from block 1106. At block 1108, a rate stable decision is made based upon preprogrammed parameters. If YES, the flow diagram returns to the HR Measurement block 1102. If NO, the rate stability information is provided to Determine Therapy and Duration block 1130.

At block 1116, thoracic impedance is continuously measured in a sampling operation. At block 1118, a MV and respiration rate calculation is made. At block 1122, a pulmonary apnea decision is made based upon preprogrammed criteria. If NO, the flow diagram returns to MV Measurement block 1116. If YES, the occurrence of apnea and MV information is provided to Determine Therapy and Duration block 1130.

At block 1124, the electroencephalogram is sensed and measured. An EEG calculation is performed at block 1126. At block 1128, a seizure episode is determined. If NO, the flow diagram returns to EEG Measurement block 1124. If YES, the occurrence of a seizure is provided to Determine Therapy and Duration block 1130.

Based upon the data presented to it, Determine Therapy and Duration block 1130 determines the type of therapy and the duration to block 1132, which controls the start of the therapy by evaluating the severity and ranking of each event (i.e., maximum ratio, duration of seizure detection, spread, number of clusters per unit time, number of detections per cluster, duration of an event cluster, duration of a detection, and inter-seizure interval). Block 1134 monitors the completion of the determined therapy. If the therapy is not complete, block returns to block 1134. If the therapy is determined to be complete, block 1134 returns the flow diagram to blocks 1102 (Measure HR), 1116 (Measure Impedance) and 1124 (Measure EEG) to continue the monitoring of cardiac, respiratory and brain signal parameters. Therapy may consist of neural stimulation, cardiac pacing, cardioversion/defibrillation, and drug delivery via a pump or any combination of therapies.

When block 1130 determines that a therapy is to be initiated Format Diagnostic Data block 1112 formats the data from the cardiac, respiration and EEG monitoring channels, adds a time stamp (e.g., date and time), type and duration of therapy and provides the data to block 1114 where the data is stored in RAM memory for later retrieval by a clinician via telemetry (using techniques discussed herein). Optionally, block 1112 may add examples of intrinsic ECG, respiration and/or EEG signals recorded during a sensed episode/seizure. Block 1115 is like block 415 in FIG. 4. Block 1120 is like block 420 in FIG. 4.

The above embodiments illustrate that the disclosed techniques may be implemented within any number of medical device systems (drug delivery, electrical stimulation, pacemaking, defibrillating, cochlear implant, and/or diagnostic) but configured to retain sensed data records in accordance with the teachings disclosed herein. In general, the implanted medical component utilizes one or more monitoring elements (e.g., electrodes or other sensors), a memory component having a plurality of data structures (and/or data structure types), a processing component (such as a CPU) to process received data for storage in memory as disclosed herein, and a telemetry component.

Data Reporting and Remote Monitoring

Figure 12:
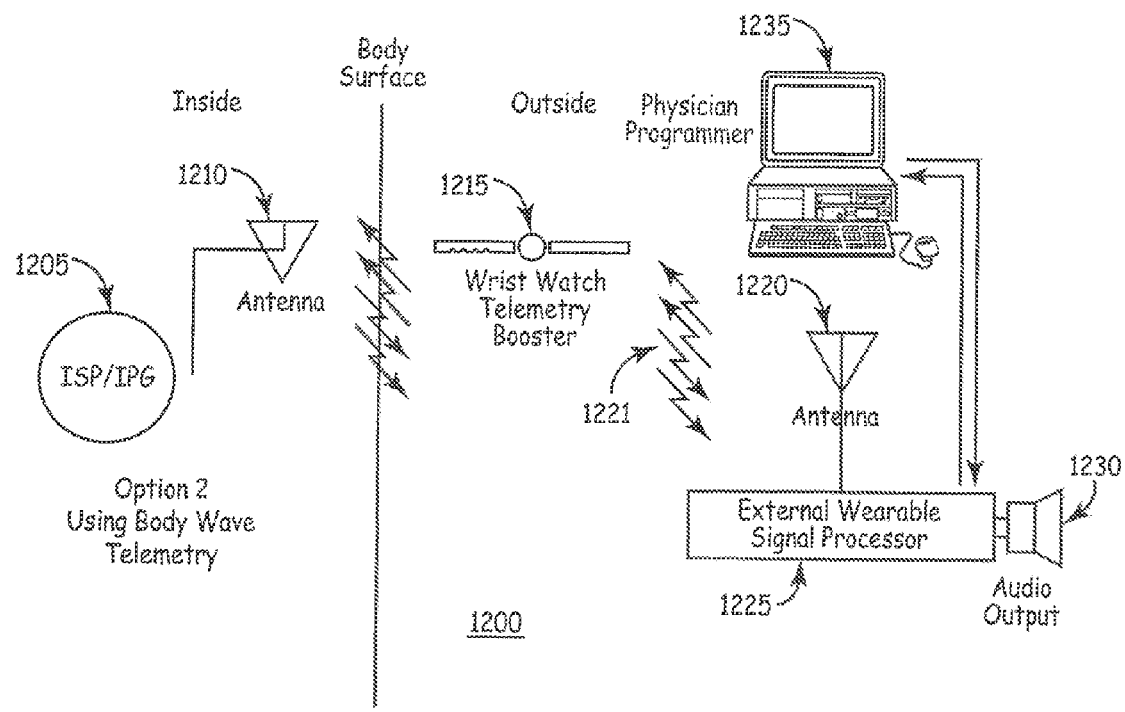
FIG. 12 shows apparatus that supports reporting neurological data in accordance with an embodiment of the invention.

FIG. 12 shows apparatus 1200 that supports reporting physiological data in accordance with an embodiment of the invention. With apparatus 1200, the implanted component 1205 of the medical device system communicates with the relaying module 1215 via telemetry antenna 1210. Similarly, the external component 1225 communicates with the relaying module 1215 via antenna 1220. In the embodiment, a telemetry link 1221 between relaying module 1215 and antenna 1220 comprises a 3 MHz body wave telemetry link. To avoid interference, the relaying module 1215 may communicate with the external and implanted components using differing communication schemes. In some embodiments, the reverse direction and the forward direction of telemetry link 1221 may be associated with different frequency spectra. The relaying module 1215 thereby provides a greater range of communications between components of medical device system. For example, in the embodiment of an implanted system, an external programmer may communicate with an implanted device from a more remote location. The external programmer may be across the room and still be in communication via the relaying module 1215. With the telemetry booster stage, the use of an implanted system is more convenient to the patient, in particular at night while sleeping or when taking a shower, eliminating the need for an external device to be worn on the body. In an embodiment, relating module 1215 may also have the features and functionality of external device 503 as shown in FIG. 5.

Figure 13:
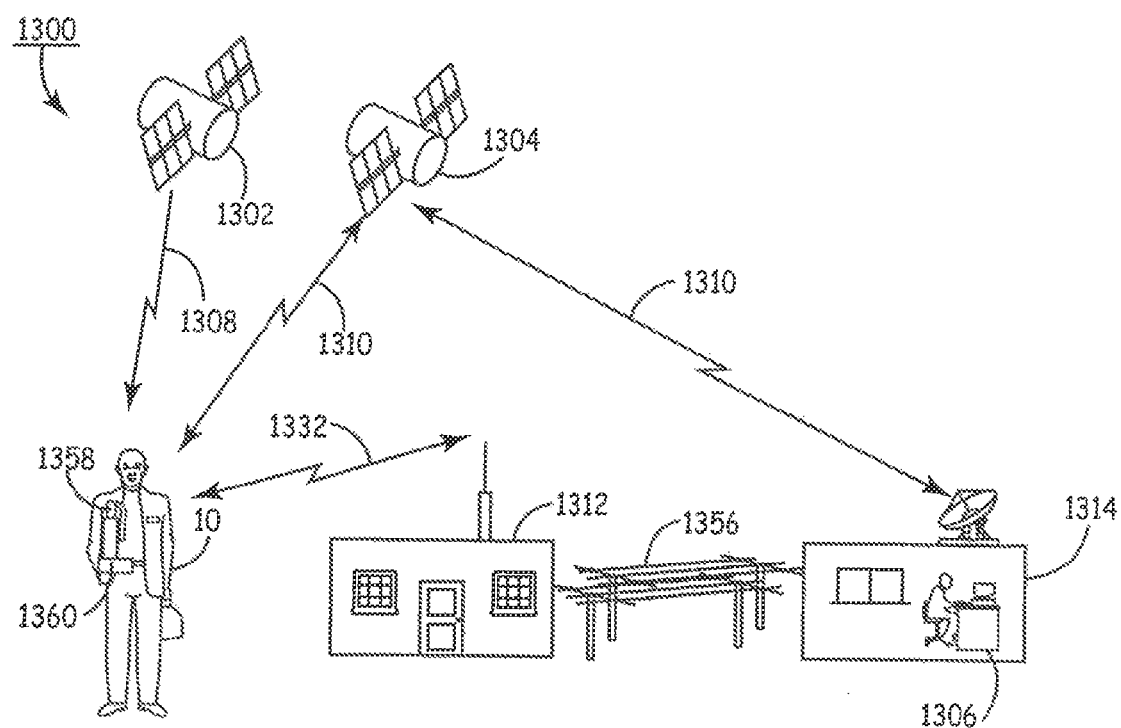
FIG. 13 is a schematic diagram of a system utilizing any of the above-described embodiments and allowing remote monitoring and diagnostic evaluation of at risk patients.

As shown in FIG. 13, in an embodiment, the system allows the residential, hospital or ambulatory monitoring of at-risk patients and their implanted medical devices at any time and anywhere in the world. Medical support staff 1306 at a remote medical support center 1314 may interrogate and read telemetry from the implanted medical device and reprogram its operation while the patient 10 is at very remote or even unknown locations anywhere in the world. Two-way voice communications 1310 via satellite 1304, cellular via link 1332 or land lines 1356 with the patient 10 and data/programming communications with the implanted medical device 1358 via a belt worn transponder 1360 may be initiated by the patient 10 or the medical support staff 1306. The location of the patient 10 and the implanted medical device 1358 may be determined via GPS 1302 and link 1308 and communicated to the medical support network in an emergency. Emergency response teams can be dispatched to the determined patient location with the necessary information to prepare for treatment and provide support after arrival on the scene. See for example, U.S. Pat. No. 5,752,976.

Figure 14:
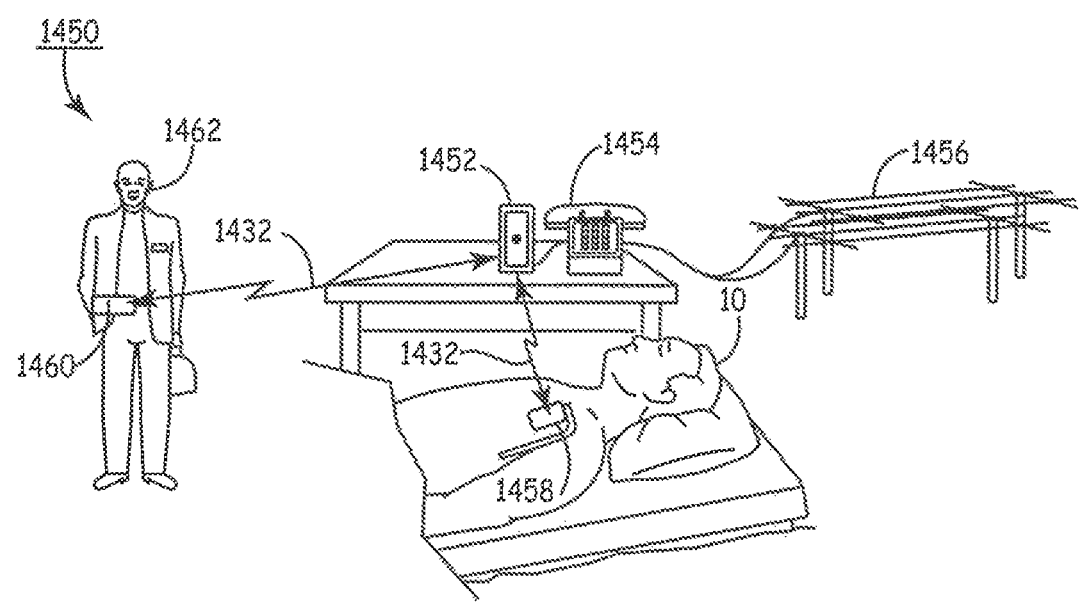
FIG. 14 is a schematic diagram of an alternative system utilizing any of the above-described embodiments and allowing remote monitoring and diagnostic evaluation of at risk patients.

An alternative or addition to the remote monitoring system as described above in conjunction with FIG. 13 is shown in the system 1450 of FIG. 14, which shows a patient 10 sleeping with an implantable Monitor 1458 and/or optional therapy device as described above in connection with the above-described systems. The implantable device 1458, upon detection of a neurologic event may alert a remote monitoring location via local remote box 1452 (as described in U.S. Pat. No. 5,752,976), telephone 1454 and phone lines 1456 or the patient's care provider via an RE link 1432 to a pager-sized remote monitor 1460 placed in other locations in the house or carried (i.e., belt worn) by the care provider 1462. The remote caregiver monitor 1460 may include audible buzzes/tones/beeps, vocal, light and/or vibration to alert the caregiver 1462 of patient's monitor in an alarm/alert condition. The RE link may include RE portable phone frequencies, power line RE links, HomeRF, Bluetooth, ZigBee, WIFI, MICS band (medical implant communications service), or any other interconnect methods as appropriate.

Each of the above embodiments utilized graphical user interfaces that are suitable for displaying data records that have been retrieved from the implantable medical device.

Data Retention and Recording Techniques

Discussed herein are techniques for selecting and storing sensed physiological data in an implanted medical device for subsequent reporting to an external device. As used herein, the term data record encompasses the sensed physiological data, summary information, or simply a pointer that references a location in memory where the sensed physiological data is stored. Thus, the concept of storage of data records in first and second data structures envisions possibilities of storage of the sensed physiological data and the storage of their associated pointers. As an example, summary information data may be stored in the first and second data structures wherein the more detailed and more space consuming waveform data (pre-detection data, post-detection data, etc.) may be stored, and pointed to, in an associated memory (such as a loop record buffer).

Mapping from entries in the first and second data structures to the waveform physiological data that is stored in the associated memory may be achieved with pointers. Each entry in the event log may point to its corresponding waveform data, or each waveform data may point to its corresponding data in the event log. Alternatively, multi-directional pointers in an "allocation table" or "allocation data structure" may be pointed to by the priority structures. Thus, when a data record is overwritten or replaced as discussed herein, both the data record itself and its mapping to the event log may be changed/removed in the allocation structure.

Figure 15:
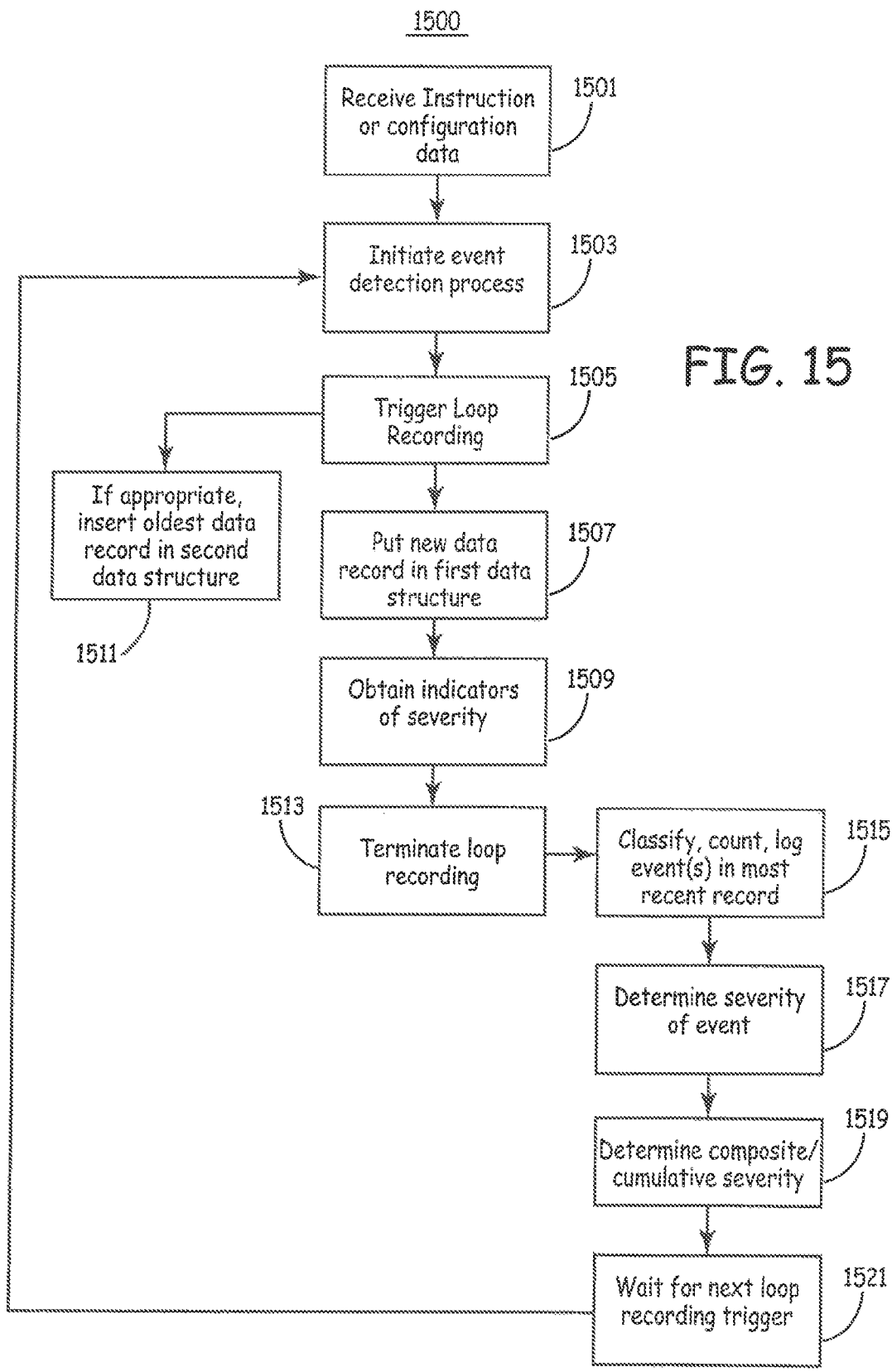
FIG. 15 shows a scenario for storing neurological data in accordance with an embodiment of the invention.

FIG. 15 shows process 1500 for storing physiological data in accordance with an embodiment of the invention. Again, the techniques disclosed herein may be implemented in any of the implantable medical device systems discussed above and may be performed in conjunction with the flow diagrams of FIGS. 4, 8, and 11 above. The process described therein may be implemented by computer executable instructions performed by a processor or dedicated hardware in the form of digital logic gates (also referred as hardware rather than software/firmware) in the implanted device. (Process 1500 may be performed by a logic component that may include a processor and/or digital logic such as an ASIC.) The process described herein discusses the storage of data records within one or more data structures and the moving of those data records. It will be appreciated, however, that these processes may be implemented by storage and movement of pointers, wherein each pointer points to data that is stored in memory, and/or the storage and movement of the sensed physiological data.

The technique for storing data records may begin with step 1501, wherein an implanted device receives an instruction or configuration data from a clinician, typically via telemetry. For example, the clinician or patient may activate loop recording to store data collected for a specified neurological event between a specified time and having a minimum severity level (as will be discussed). In step 1503, an implanted device initiates a detection process for a neurological event. This detection process may implement an event detection algorithm to process the sensed physiological data and determine the possible onset of a neurological event. The neurological event may be associated with a nervous system disorder (e.g., an epileptic seizure) having a severity level and a time duration. The neurological event may also be a cardiac event. For example, a patient's heart rate may increase with an occurrence of an epileptic seizure. Accordingly, the implanted device may initiate loop recording upon determination of a neurological event by processing of sensed physiologic signals or upon determination of any number of other criteria.

By way of example only, the system may monitor one set of physiological signals (e.g., EEG) and trigger loop recording of those same signals upon detection of a neurological event. As another example, the system may monitor any combination of a plurality of physiological signals (including EEG, respiratory, and cardiac) and trigger loop recording of only a subset of those physiological signals based on predetermined criteria being satisfied with respect to one or more of the other physiological signals.

In an embodiment, the implantable medical device may have a set of monitoring elements sensing brain activity and another set of monitoring element that sense a physiological activity other than the brain (e.g., heart activity such as a heart arrhythmia and/or respiratory activity). The device may then implement a detection algorithm to determine the possible onset of a possible neurological event (e.g., a seizure) based on the sensed signals from either the first or second monitoring elements. Once a neurological event is detected, data records associated with the first and second monitoring elements may be stored in memory in accordance with the teachings herein.

Alternatively or additionally, the device may initiate loop recording upon indication to do so by the patient based, for example, on a patient detecting a neurological event. In the event the patient initiates loop recording based on detection of a neurological event (wherein, however, the detection process of the implanted device has not detected the neurological event), the priority index (discussed below) for such data may be set at a higher level such that the data is stored in a memory. In the situation where the patient experiences a neurological event but the medical device has not detected the event, the physiological sensed data may be particularly important for storage and subsequent evaluation. In an embodiment, once activated by a patient, loop recording may save the data for 30 seconds before the indicated seizure and 3 minutes after the seizure. However, to allow for the fact that the patient may not mark the seizure until the seizure has ended, the ECG loop recording may begin 3 to 5 minutes before the patient mark. This time period may be programmable. As discussed below, a subset or a composite of physiologic channels is selected from the available physiologic channels based on a selection criterion.

Referring still to FIG. 15, if the detected neurological event meets the criterion provided by the clinician, the system triggers loop recording in step 1505. In step 1507, the implanted device stores a data record associated with the sensed physiological data in a first data structure (in an embodiment, a circular buffer as will be discussed in greater detail in FIG. 16). Again, the data record may either be a pointer or the physiological data. An exemplary data entry is discussed below in relation to FIGS. 18 and 19. In an embodiment, the circular buffer stores chronologically sequenced data records in sequential memory locations. When the last location in the circular buffer is reached, the next data record is entered in the first memory location of the circular buffer. Although the embodiment of FIG. 15 and the corresponding discussion herein is with respect to a circular buffer, it will be appreciated that the circular buffer may be any memory device or structure and the data records may be stored and replaced according to an associated priority index (discussed below). When the memory device is full, any new data may replace data in the memory device having the lowest associated priority index. Alternatively, as discussed below, the data may be automatically transferred out once the priority index is calculated.

With the storage of neurological data in step 1507, the implanted device may also obtain and retain indicators of severity when the neurological event occurs in step 1509. Examples of retained indicators include a maximum value of foreground ictal severity and heart rate during the neurological event. Indicators of severity are discussed further below and may be used to determine a priority index.

If the first data structure becomes full, a new data record replaces either the oldest data record or the existing data record having the lowest associated priority index. However, in step 1511, if the associated priority index of the data record being replaced by the new data record is sufficiently large, the data record being replaced may be stored in a priority buffer instead of being permanently removed. It will be appreciated, that the data records may vary in size. Accordingly, for a new data record having a sufficiently large size, the system may require multiple old data record to be removed. Alternatively, only the least important portions of the data record would need to be removed from the first data structure.

The priority index of a data entry, discussed next, is determined in steps 1515, 1517, and 1519 in concert with clinician input and information obtained by the implanted device. In the embodiment of the invention, steps 1507, 1509, and 1511 are executed in a parallel manner. In step 1513, the recording of neurological and other physiological data in the circular buffer is completed, in an alternative embodiment, the data entry may be transferred from the first data structure (such as the circular buffer) to the second data structure (priority buffer) upon the priority index of the data entry being determined. In such an embodiment, the second data structure may begin to be populated with data records without requiring for the first data structure to become fill and start replacing older data entries. Since the stored data entry is promptly removed to the second data structure, the circular buffer may vary in size.

One embodiment for determining the priority index of a data record is as follows. In step 1515, the most recent data record is classified. For example, the neurological event may be classified as an epileptic seizure. In step 1517, a priority index of the neurological event is determined. The priority index may be dependent on a severity level. In an embodiment, the severity level is a function of at least one characteristic of the neurological event, including the duration, spread, and measure of ictal content (e.g., peak ratio of algorithmically derived foreground to background ictal score) of the neurological event. Moreover, the embodiment may utilize other derivative indicators for determining the severity level. For example, a binary evidence count may be determined in which each new sample is compared to a criterion (e.g., a threshold determined by the product of a background value and a configured threshold value). If the criterion is met, a value of "1" is inserted into a data structure that contains Y previous Boolean values. Otherwise, if unmet, a value of "0" is inserted into the data structure. Upon insertion, a second value is removed from the data structure to ensure that the data structure retains a size of Y bits. The Boolean value of the first sample is then compared to the Boolean value of the second sample. The difference is used to maintain a separate counter value which reflects how many Boolean values in the data structure (e.g., Y-bit buffer) are "1". In this way, the evidence count reflects the number of samples out of the last Y samples which met the threshold criterion, and therefore ranges from 0 to Y.

As another example, a slew-rate limited output of an associated physiologic channel may be determined by incrementing the slew-rate limited output by a small amount if the sample is greater than the current value of the slew-rate limited output. Otherwise, the slew-rate limited output is decremented by the small amount. The severity level may be determined from the maximum value of the evidence count or the slew-rate limited output associated with the set of physiologic channels contained in a data record.

In addition, the priority index of the neurological event may be dependent on an associated event, e.g., a cardiac event or a user signal in the form of telemetry, presence of a medical magnet, and so forth. In an embodiment, the priority index is stored in a data field in the data record. However, another embodiment of the invention may store the priority index in an associated data structure or may be calculated when it is needed.

In step 1519, a composite severity measure of a group of neurological events, which includes the current neurological event, is determined. The composite severity measure may be a function of determined severity levels of individual events and the relative chronological occurrence of events. For example, a group of epileptic seizures that occur within a short period time may be indicative of a more significant cumulative event than a single epileptic seizure.

While the embodiment illustrated in FIG. 15 shows a sequential ordering of steps, it will be appreciated (as discussed above) that the process may execute the steps in a different order or may execute some of the steps in a parallel fashion.

The priority index may be dependent on the severity level, which may be expressed as a function $f(x_1, x_2, \ldots, x_n)$, and/or on associated factors, which may be expressed as a function $g(y_1, y_2, \ldots y_m)$. Variable $x_i$ corresponds to a characteristic of a physiologic event (e.g., a neurological event), and variable $y_j$ is an associated factor. For example, characteristics of a neurological event may include a duration of a neurological cluster, a spread of a neurological cluster (which may be measured by the number of electrodes detecting the cluster), a statistic of an associated neurological signal, and an event class. A statistic may be a computed quantity characteristic of a physiologic signal or an ensemble of physiologic signals. An event class may include a most-severe seizure (potentially correlating to status epilepticus), a severe seizure, a sub-clinical seizure, a least severe seizure (potentially correlating to what is more likely to be an erroneous detection), a brady event, a tachy event, arrhythmia, and a detection on each electrode channel.

An associated event may include external event information and associated physiologic information that are correlated to a neurological event. For example, the associated physiologic information may be the age of the event. As another example, an external event may be a cardiac event, a chemical event, a scheduling event, a patient-initiated event (through a physical interface, e.g., a magnet interface or a telemetry interface), a caregiver-initiated event (e.g. through a telemetry channel), and a device-based event. Associated physiologic information may include heart rate, blood pressure, breathing rate, and glucose level. Moreover, an external event may not be associated with a neurological event. For example, a physician may instruct, through a programmer, that physiologic data for a designated time be stored and reported.

The priority index may be expressed as a mathematical combination of the severity level function $f(x_1, x_2, \ldots, x_n)$ and the associated factor function $g(y_1, y_2, \ldots y_m)$. For example, the priority level may be expressed as:

$$\text{priority index} = f(x_1, x_2, \ldots, x_n) + g(y_1, y_2, \ldots, y_m) \quad \text{(EQ. 1A)}$$

Either $f(x_1, x_2, \ldots, x_n)$ or $g(y_1, y_2, \ldots y_m)$ may be a continuous function, a discrete-value function, a Boolean function, or a combination of the above function types. As another example, the priority level may be expressed as:

$$\text{priority index} = f(x_1, x_2, \ldots, x_n) \cdot g(y_1, y_2, \ldots, y_m) \quad \text{(EQ. 1B)}$$

The Priority Index May be More Generally Expressed as a Function $h(z_1, z_2)$, where $$\text{priority index} = h(f(x_1, x_2, \ldots, x_n), g(y_1, y_2, \ldots, y_m)) \quad \text{(EQ. 1C)}$$

Figure 16:
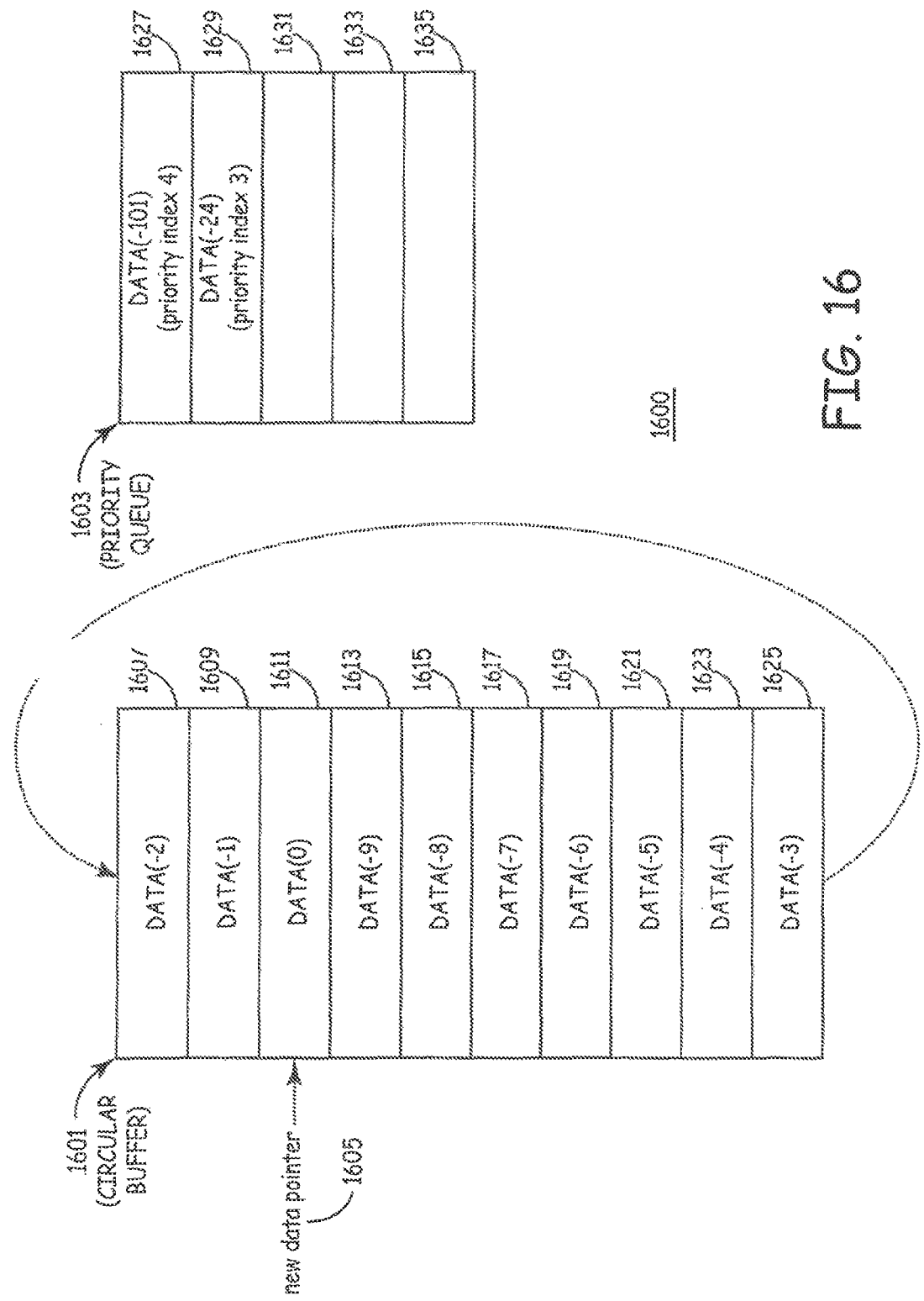
FIG. 16 shows a data structure for storing neurological data in accordance with an embodiment of the invention.

FIG. 16 shows data structure 1600 for storing physiological data in accordance with an embodiment of the invention. In this embodiment, data structure 1600 includes circular buffer 1601 and priority queue 1603. (Another embodiment of the invention may implement circular buffer 1601 and/or priority queue 1603 as a different type of data structure.) Circular buffer 1601 stores the most recent ten data records (DATA(-2) to DATA(-3)) corresponding to data entries 1607-1625). (An exemplary record is discussed with FIG. 18.) However, the embodiment may store a different number of data records, depending on the allocated memory for circular buffer 1601. In the example shown, circular buffer 1601 currently stores data records that have been acquired between the previous nine time units (corresponding to data record DATA(-9)) and the current time (corresponding to data record DATA(0)). New data pointer 1605 points to a data entry in circular buffer 1601. At the current time, new data pointer 1605 points to the data entry where new data is stored. Previous to storing data record DATA(0), data entry 1611 stored data record DATA(-10), which was previously acquired 10 time units ago. The new data record may be associated with physiologic signals and may be further associated with a neurological event. With the next subsequent data acquisition, new data pointer 1605 will point to the next data entry that currently stores data record (DATA(-9)). In the embodiment, the new data record is stored in the data entry that stores the oldest data record. When last data entry 1625 (currently corresponding to data record DATA(-3)) of circular buffer 1601 is reached, the subsequent data acquisition is stored in data entry 1607 currently storing data record DATA(-2).

As discussed, the data record may be the sensed physiological data or a pointer that references a location in memory where the sensed physiological data is stored. Thus, the concept of storage of data records in first and second data structures envisions both possibilities of storage of the sensed physiological data and the storage of their associated pointers. Also as discussed, circular buffer 1601 may be in the form of any other data structure. In such an alternative embodiment, physiological data may be stored in a memory device such that when a new data record is to replace an existing data record, the data record with the lowest priority index is replaced. Alternatively, the data entries being replaced may vary depending on the relative sizes of the new and old data entries.

When a data record has been overwritten by the new data record, a portion of the old data record (which may be the entire data record) is stored in priority queue 1603 if the corresponding priority index is sufficiently large or exceeding a threshold criterion. In one embodiment, the more significant the corresponding physiologic event, the larger the corresponding priority index. However, in another embodiment the priority level may decrease with the significance of the physiologic event. Priority queue 1603 is capable of storing data records in data entries 1627-1635; however, as shown in the example, priority queue 1603 currently stores two data records. The remaining data entries 1631, 1633, and 1635 are empty and may store subsequent data acquisition. Data entry 1627 is currently storing data record DATA(-101), which was acquired 101 time units ago, and data entry 1629 is currently storing data record DATA(-24), which was acquired 24 time units ago. For example, the priority index must have a value of 3 or higher in order to be stored in priority queue 1603 when the corresponding data record is overwritten in circular buffer 1601. In the event that the priority queue 1603 is also filled, the system may determine that a data record shall be retained in priority queue 1603 only if the priority index of the removed data record from circular buffer 1601 has a larger priority index than any of the stored data entries in priority queue 1603. In other embodiments, the system may utilize a combination of the above retention strategies or other strategies.

In an embodiment of the invention, a data record (stored in data entries 1607-1625 1607, 1609, 1611, 1613, 1615, 1617, 1619, 1621, 1623, and 1625) in circular buffer 1601 may contain a different amount of data than a data record (stored in data entries 1627-1635 1627, 1629, 1631, 1633, and 1635) in priority queue 1603. For example, data may be discarded to reduce the precision or to discard physiologic data that is not directly associated with a neurological event (e.g., cardiac data).

In an embodiment of the invention, stored data (either stored in circular buffer 1601, or priority queue 1603, or both)

may be selected in accordance with a retention policy in order to support intelligent data loss (data triage) or offloading (e.g., to an external device) and to conserve memory usage and reduce/bound the time required to transfer the data. For example, an implanted device may store data in data structure 1600 for sensor channels fulfilling a predetermined criteria, may discard waveform data while retaining statistics, summary data, or burden information, enable or disable or prioritize sensor channels based on algorithm criteria, sensor location, or sensor type, or override the retention policy when a clinician provides instructions over a telemetry channel. Moreover, the embodiment may further use data compression if the data is compressible to compress the data content of the new or old record.

Reporting Physiological Data

In accordance with another aspect of the invention, in response to an instruction from a clinician, an implanted device organizes stored physiological data according to the associated priority index and reports a predetermined number of data records that are deemed as having a higher priority index than the other stored data records. Such structures for reporting stored physiological data are disclosed in FIGS. 12-14.

Figure 17:
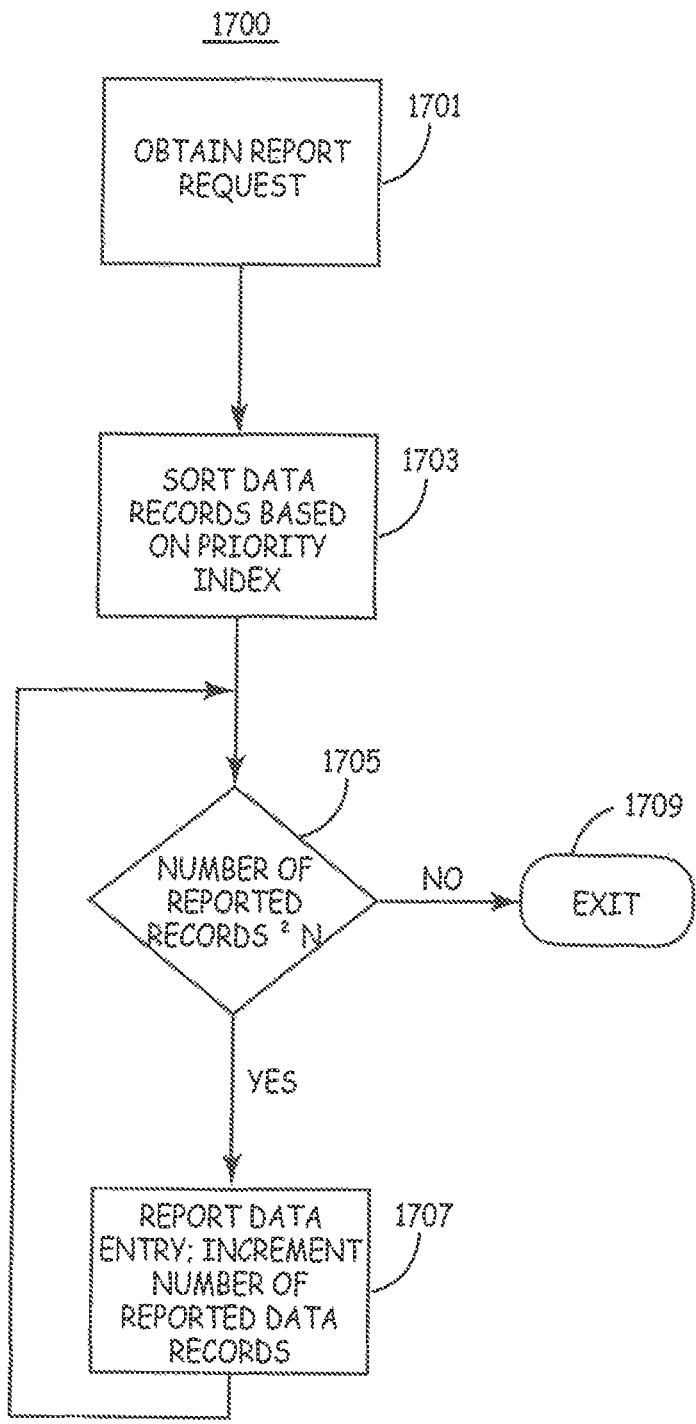
FIG. 17 shows a flow diagram for reporting neurological data in accordance with an embodiment of the invention.

FIG. 17 shows flow diagram 1700 for reporting physiological data in accordance with an embodiment of the invention. Step 1701 corresponds to an implanted device receiving a request (e.g., through a telemetry communications channel). In step 1703, the data records (both in circular buffer 1601 and priority queue 1603) are sorted according to the associated priority index if the associated priority index is sufficiently large (e.g., three or higher). Step 1705 determines if the number of reported data records is less than or equal to N. N can be, for example, the number of records that the user wishes to retrieve. If so, the physiological data associated with the data record is reported to a clinician's workstation over the telemetry communications channel and the number of reported data is incremented in step 1707. Step 1705 is then repeated. If the number of records is greater than N, the reporting of neurological data is terminated in step 1709, and procedure 1700 is completed.

A physician may request physiological data associated with N data records that are stored in circular buffer 1601 and priority queue 1603 and having a minimum priority index to be reported to, for example, a physician programmer over a telemetry link. The physician programmer may thereby display the requested physiological data or at least those where the priority index is above a threshold. When so instructed, implanted device sorts the physiological data associated with the data records in circular buffer 1601 and priority queue 1603 and reports physiological data associated with the N data records having at least the minimum priority index. Once the data is reported, the implanted device may release the memory space previously allocated to the identified data records, mark that memory space for deletion, and/or delete the data records. If more than N data records have the minimum priority index, the implanted device may select N data records based on a temporal criterion (e.g., the most recent or the oldest), being greater than a predetermined priority index, or a priority index that is dependent on an external event. Moreover, system may select a data record so that each occurring event type is included in the reported data records. Because the invention may be implanted within any implantable medical device system, however, it will be appreciated that the external components may vary in configuration, components and/or features.

Data Format

Figure 18:
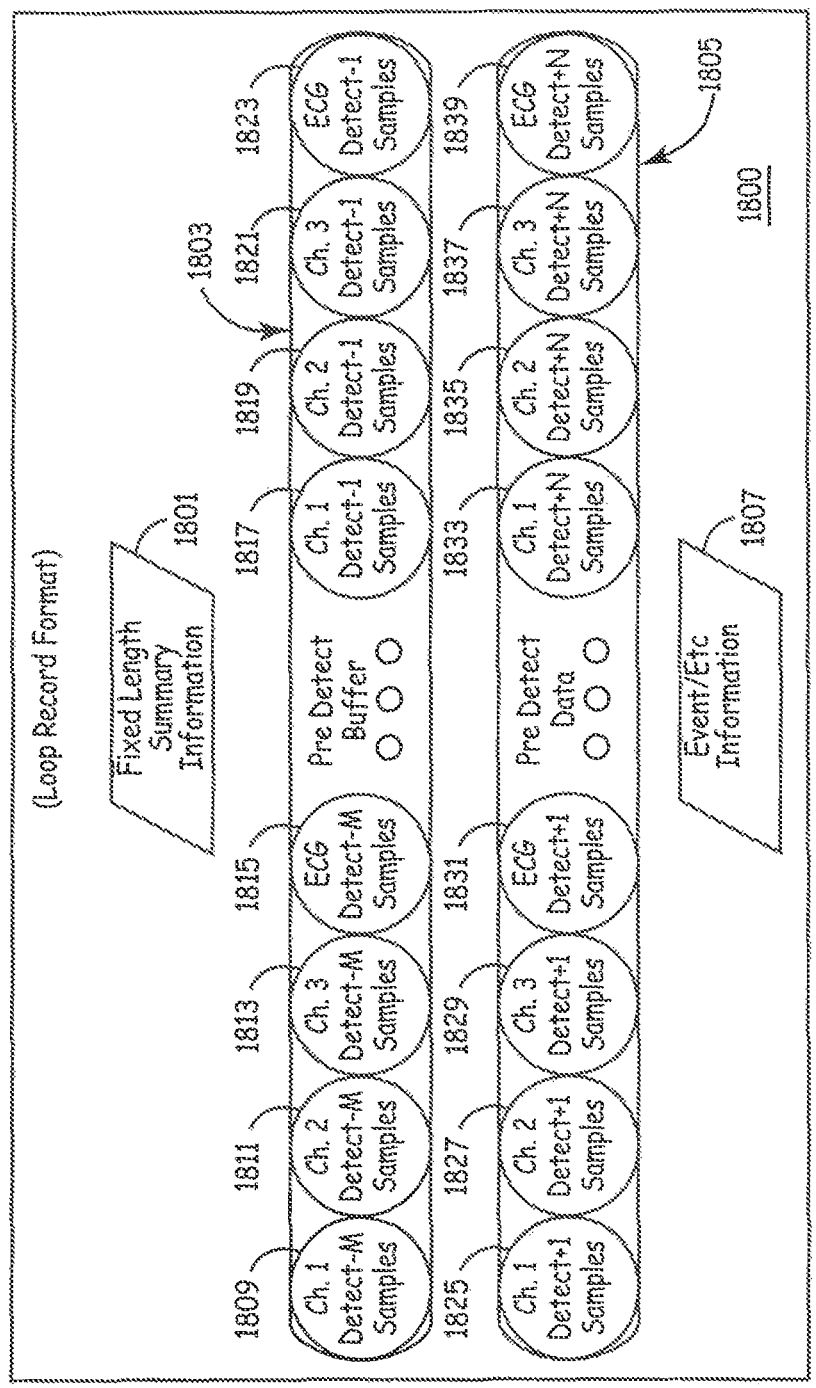
FIG. 18 shows an exemplary data entry that contains physiologic, data and that may be retained in memory of an implantable medical device.

FIG. 18 shows exemplary physiological data 1800 that can be retained in implanted medical device. The physiological data 1800 comprises summary information data 1801, pre-detection data 1803, post-detection data 1805, and event/etc information data 1807. Pre-detection data 1803 contains sampled data 1809-1823 1811, 1813, 1815, 1817, 1819, 1821, and 1823 that is collected before a detected physiologic event such as an epileptic seizure. Post-detection data 1805 contains sampled data 1825-1839 1825, 1827, 1829, 1831, 1833, 1835, 1837, and 1839 after the detected physiologic event. In the exemplary data shown in FIG. 18, pre-detection data 1803 includes sampled data 1809 and 1817 that are obtained from neurological channel 1, sampled data 1811 and 1819 that are obtained from neurological channel 2, sampled data 1813 and 1821 that are obtained from neurological channel 3, and sampled ECG data 1815 and 1823 that are obtained from the ECG channel. Post-detection data 1805 includes sampled data 1825 and 1833 that are obtained from neurological channel 1, sampled data 1827 and 1835 that are obtained from neurological channel 2, sampled data 1829 and 1837 that are obtained from neurological channel 3, and sampled data 1831 and 1839 that are obtained from the ECG channel. While the physiologic channels sampled before and after the physiologic event are same in exemplary record 1800, different physiologic channels may be sampled before and after the physiologic event. Additionally, summary information data 1801 contains summary information about record 1800. The embodiment of the invention supports physiological data that has a fixed length or that has a variable length. Event/Etc information data 1807 includes information about the associated physiologic event type and other associated information. Although depicted as data from different channels interleaved together, such data may also be stored in a non-interleaved fashion. For example, ECG may be stored separately from the other channels, etc.

Figure 19:
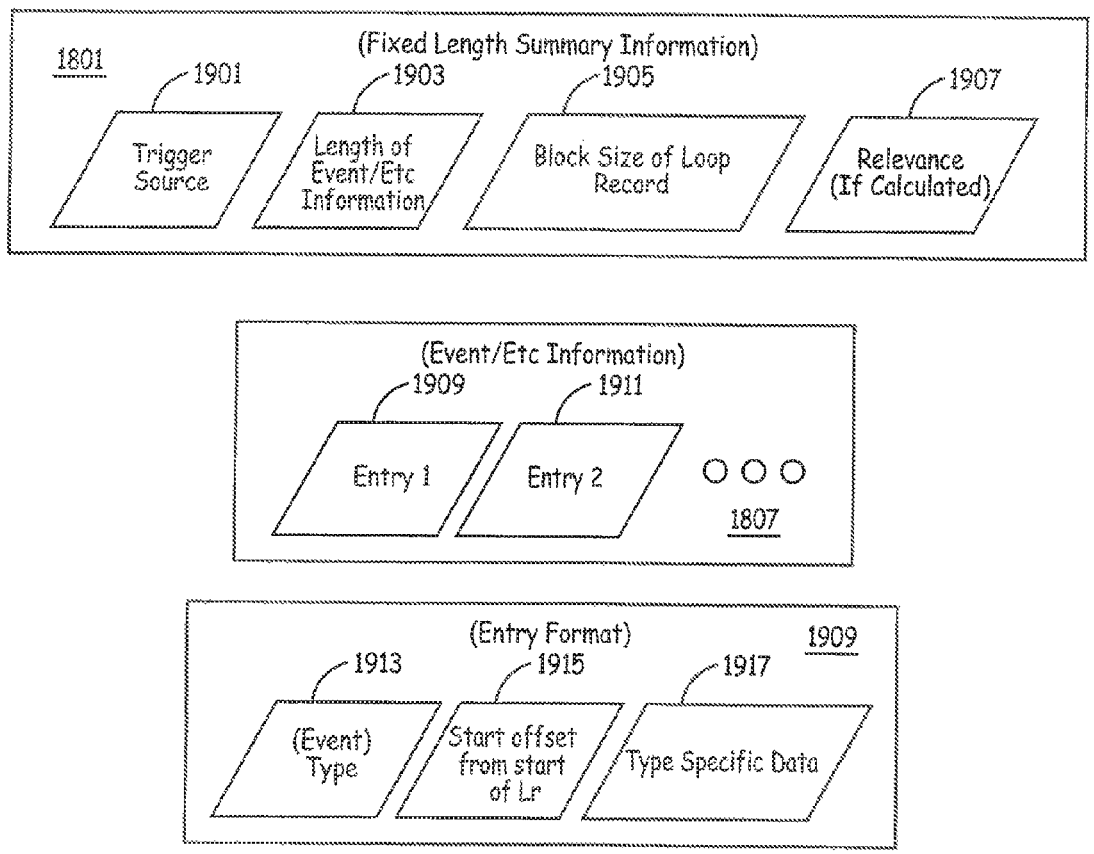
FIG. 19 shows components of the exemplary data entry as shown in FIG. 18.

FIG. 19 shows components of the exemplary physiological data as shown in FIG. 18. Summary information data 1801 includes trigger source data 1901, length of event/etc information data 1903, size of loop record 1905, and relevance information 1907. Trigger source data 1901 identifies what triggered recording (e.g., a neurological channel number). Length of event/etc information data 1903 is indicative of the length of event/etc data 1807, size of loop record 1905 contains the length of record 1800, and relevance data 1907 indicates the relevance level of each sampled channel as will be later discussed. Event/Etc information 1807 contains entries 1909 and 1911. Each entry includes event type 1913 that is indicative of an event associated with record 1800, start offset data 1915 includes the offset of record 1800 from the start of the loop recording, and type specific field 1917 includes specific data that is associated with the event. (However, in an embodiment of the invention, a data entry may store a pointer to physiologic data rather than store the physiologic data itself.) Record 1800 may be associated with a plurality of event types, each being indicated in separate entries, e.g., entries 1909 and 1911.

Data structure 1600 (as shown in FIG. 16) typically can store 1 to 16 Mbytes of data. Record 1800 may contain anywhere from approximately 5 Kbytes to approximately 1 Mbyte. Typically, a record contains 30-90 Kbytes per record. The embodiment supports both fixed size records (e.g., 60 Kbytes) or variable size records. With variable size records the retention scheme, as previously discussed, may require that a plurality of records or only portions of records be removed from circular buffer 201 in order to store a new record. Also, different parts of a record may be stored in physically different memory components (e.g., summary/header information data 601 in one place (a log) and sampled data 1803 and 1805 in another (waveform memory) with a pointer in the header/summary information indicating where the start of the data is and how much data is there).

As discussed, in an embodiment of the invention, a data record may be a pointer to physiologic data rather than store the physiologic data itself. Thus, for example, summary information data 1801 and/or event/etc information data 1807 may be stored in the first and second data structures wherein some or all of the entries may be mapped, via pointers, to more detailed and more space consuming waveform data (pre-detection data 1803, post-detection data 1805) in an associated memory (such as a loop record buffer).

Selective Storage of Data Channels

The embodiment supports the generation of records at different rates. The record rate will vary widely with an implanted device's configuration and with the patient. For example, a clinician may desire to record every detected seizure over a time period. There are some patients that have 1 seizure every 6 months, but there are some that have 500 seizures a day. A typical patient may have 2 unique events (seizure, button press, etc) per day.

While FIG. 18 shows an exemplary configuration with three neurological channels and an ECG channel, an embodiment of the invention supports a variable number of neurological channels so that the memory of an implanted device can store necessary information over a desired period of time. The channels may be adjusted either in quasi-static manner or in a dynamic manner. In an embodiment, the implanted medical device contains a channel selection component, which may be software or hardware logic for performing a process of selecting the one or more channels for data storage as described herein. An evaluation processing component may thereby obtain the selected channel data and process the channel data also in accordance with the techniques described herein.

For applications like the detection of epileptic seizures and the subsequent recording of data, it is advantageous, from a quality and resource stand-point, to be able to select a subset (which may include all physiologic channels) of the sensed input channels for detection processing and/or loop-recording. While this can be done manually prior to the availability of relevant data by defining the selected channels, manual configuration is less flexible and less desirable than allowing the closed-loop, real-time, quasi-real-time, periodic, or otherwise automated selection of physiologic channels.

With implantable detection algorithms and applications, there are typically a multitude of input sense channels. The degree of interest for each of these sense channels is often discernable while an implanted device is collecting data and storing the data in a memory component, e.g., a memory structure. As each sample is processed or stored as a short recording of samples, an application specific method may be employed to identify the most interesting (relevant) physiologic channels. Samples from selected physiologic channels may be utilized. Detection processing is typically resource intensive such that all physiologic channels may be utilized. Data recording in a loop-recording rapidly fills memory and then later prolongs telemetry. In order to effectively process and store the samples, judicious selection of physiologic channels may be desired.

With a detection algorithm operating on physiological signals, it is likely that simply obtained information may reveal which channels to retain or continue processing. Often, physicians/users may be interested in examining, using, and retaining data from the physiologic channels in which an indication of an event is present. For example, if a seizure is detected on two of eight detection channels of data being recorded from the brain, only those two neurological channels need be retained. In this example, the savings in storage may be significant since only two channels are kept and six neurological channels are discarded, corresponding to a 4 to 1 sample compression.

Sample compression may be important if memory of an implanted device is limited. In the above example, one needs to decide which two channels should be kept. The decision may be based upon a number of factors including, independently-calculated channel severity (e.g., save the most severe), channel event onset time (e.g., save the first to detect), and seizure burden indication on the physiologic channel. In such a scenario, the flow diagram of FIG. 15 may be modified such that a severity calculation is performed prior to actual storage of the data in the first data structure. Or stored data records may be automatically removed from those data channels that are determined that the data is not important. Similarly, this approach may be extended to different and mixed physiologic signals. For example, if the multiple EEG channels are being polled, one may keep only those EEG channels where the neurological event data is most important (e.g., based on a severity scoring). If both cardiac, intra-cranial pressure (ICP) and EEG channels are being polled, one may keep only the signal types that deviated from norm. If the intra-cranial pressure rises significantly, one may keep samples from the ICP channel. If the previous scenario occurs while there is a tachycardia event, one may further keep samples from the ECG channel. Furthermore, if a seizure occurs near the same time, one may keep samples form all three channels.

The above approach may be extended to include the retention of more than one channel from a channel list sorted by relevancy as determined by a function of various factors (e.g., onset time, presence and severity of an event) as previously discussed. One may keep the most relevant physiologic channels of the channel list. For example, one may keep the three most relevant ("interesting") physiologic channels of five physiologic channels. Keeping the two or most relevant physiologic channels is referred as the "multi-max" of the channel list.

Alternatively, the system may retain a composite signal, which may be, for example, the sum of a plurality of channels. Other embodiments of the invention may utilize other derivatives. Furthermore, the channels themselves may be down-sampled or precision-reduced so that, for example, the least relevant samples are kept at 16 times less precision in amplitude and 2 times lower sampling rate resulting in about 4 times smaller data size.

Furthermore, with seizure detection and many other neurological applications the most interesting physiologic channels may be identified as those physiologic channels that are associated with the maximum energy value, normalized energy value, severity, or energy approximated value in the applications seizure frequency domain. For seizure detection, the seizure frequency domain may be 5-70 Hz (more narrowly this is typically 5-45 Hz) or (for fast ripple detections) at very high frequency (approximately 200 Hz or more). The energy value may often be sampled as the "rectified" (absolute value, square, etc.) of the samples taken directly from the filtered EEG signal. While this data may constantly be higher in some neurological locations, it is useful to normalize the data across the physiologic channels with manual or automatic gain control. Automatic gain control may be implemented as the daily comparison of running 1-pole filters and with the appropriate adjustment in response or in some other manner. For example, the gain of each physiologic channel may be adjusted so that the associated background signals are similar (to each other and/or to a target value), which may be referred to as background normalization. Because short signals may appear similar to interesting material over the short term, it is useful to smooth or reject outliers from the energy signals before comparison. Smoothing may be done, for example, using 1-pole filters, voting schemes, running or block percentile filters, percentile tracking technologies or slew-rate limiters to eliminate or mitigate, for example, the effect of epileptiform discharges (ED's) and sleep-spindles.

The embodiment supports different criteria for selecting channels for retention from a set of N physiologic channels. Different selection criteria include Max, MultiMax, MaxDeviationRetention, and Time-Distributed Max, MultiMax or MaxDeviation criterion. With the Max criterion, the physiologic channel with the highest energy is selected. With the MultiMax criterion, the M of N physiologic channels with the highest energy signals are selected. The selection may be implemented in a number of approaches, including multiple passes and sorting techniques. With the MaxDeviationRetention criterion, the physiologic channel with the highest energy is selected (as with the Max criterion). Moreover, P additional physiologic channels are selected that have an energy value greater than a determined fraction of the highest energy value. Variations of the above three criteria (Max, MultiMax, and MaxDeviation) may formed by selecting instantaneous values or by processing the physiologic channels with a window function. When determining a processed value, a physiologic channel maybe selected based on a configurable long to very short-term running window. The window may be based on any number of criteria including without limitation one or more of the following: median (or other percentile) of the window; mean of the window; running 1-pole value (e.g., one for each physiologic channel in which an associated time constant defines the width of an "effective" window); and accumulated absolute differences sum/accumulation (i.e., line-length). The accumulated difference criterion accumulates the difference of all channels with respect to a selected zero-channel. If there are accumulations greater than zero, the largest of those physiologic channels is selected.

With an embodiment of the invention, the selection of physiologic channels may occur after filtering (e.g., band-pass, notch, FIR, and IR) the physiologic channels. For example, an EEG signal may be filtered in the 10-60 Hz range to remove the bulk of the EEG energy content that may otherwise mask the ictal content. As another example, the physiologic channels may be filtered in the 180-250 Hz range in order to study "fast-ripple" events.

The above channel selection process is applicable both for records stored in circular buffer 1601 and priority queue 1603. Moreover, the channel selection criterion for circular buffer 1601 may be different from the channel selection criterion for priority queue 1603. In an embodiment of the invention, a "channel compositing" process is supported. A physiologic data sample is obtained from each of a subset of physiologic channels at an approximate time instance. For example, an implanted device may interface with N physiologic channels. A first subset of physiologic channels may include the first N/2 physiologic channels, a second subset may include the next N/2-1 physiologic channels, and a third subset may include the last physiologic channel. (A subset of physiologic channels may include all physiologic channels, one physiologic channel, or some number of physiologic channels in between.) Physiologic channels may be grouped into subsets in accordance different criterion, including the proximity of electrodes and the associated physiological functionality. A composite data may be determined from the sampled data of each subset of physiological data and stored in a data record. For example, the composite data may be the median value of the sampled data for the associated subset of physiologic channels. The embodiment may determine the composite data by other ways. For example, the minimum value, the maximum value, or the variation among the associated physiologic channels may be used. Also, the composite data may include a mixture of a plurality of physiologic data samples in a subset, e.g., a sum of selected physiologic data samples or a ratio of the largest physiologic data sample to the smallest physiologic data sample. Composite data is stored in a data record for each subset of physiologic channels.

Figure 20:
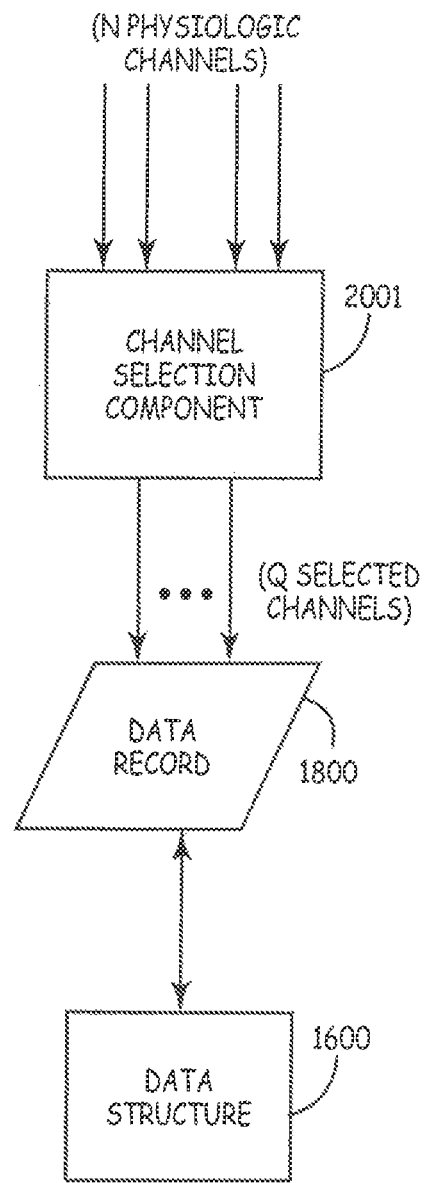
FIG. 20 shows the selection of channel data for retention in a data structure.

FIG. 20 shows the selection of channel data for retention in data structure 1600. In the embodiment, channel selection component 2001 and data structure 1600 are supported by an implanted component. Channel selection component 2001 obtains N physiologic channels from various sensors that may include neurological signals, EEG signals, and a mixture of physiologic signals. Channel selection component 2001 selects a subset of physiologic channels from the N physiologic channels using a selection criterion as previously discussed. Data from the selected physiologic channels is included in record 1800. Moreover, the selected physiologic channels may be processed by the implanted device and/or stored into memory. The embodiment, as shown in FIG. 20, stores record 1800 into data structure 1600 as previously discussed. Similarly, the above approach may be extended to different and mixed physiological signals.

In the embodiment, channel selection component 2001 includes a channel processor that selects a subset of physiological channels using the selection criterion. The channel processor may be implemented with a microprocessor, a signal processor, or other processor means.

As can be appreciated by one skilled in the art, a computer system with an associated computer-readable medium containing instructions for controlling the computer system can be utilized to implement the exemplary embodiments that are disclosed herein. The computer system may include at least one computer such as a microprocessor, digital signal processor, and associated peripheral electronic circuitry.

Thus, embodiments of the invention are disclosed. One skilled in the art will appreciate that the above teachings can be practiced with embodiments other than those disclosed. The disclosed embodiments are presented for purposes of illustration and not limitation, and the inventions are limited only by the claims that follow.

What is claimed is:

1. A method of selective data retention in an implantable medical device, the method comprising:
   sensing a neurological event that includes ictal content;
   creating a data record of the neurological event that includes the ictal content;
   determining a severity level of the neurological event by analyzing the ictal content;
   storing the data record in a data structure containing a plurality of data records, the plurality of data records representing information about a plurality of neurological events;
   determining a priority index for the plurality of data records based on severity levels of the determined neurological events where the higher the severity level the higher the priority index; and
   once the data structure is full, selectively replacing an existing data record in the data structure with a newer data record that has a higher priority index than the existing data record.

2. The method of claim 1, wherein the severity levels of the neurological events are based on a duration of the determined neurological events.

3. The method of claim 1, wherein the severity levels of the neurological events are based on a peak ratio of foreground to background ictal content of the determined neurological events.

4. The method of claim 1, wherein the severity levels of the neurological events are based on a spread of ictal content of the determined neurological events.

5. The method of claim 1, wherein storing the data record comprises initiating a loop recording upon detection of the neurological event.

6. The method of claim 5, wherein initiating loop recording occurs upon detection of a seizure.

7. The method of claim 1, wherein storing the data record comprises initiating loop recording upon manual user activation in response to a patient experiencing the neurological event.

8. The method of claim 1, wherein the data structure is present within a circular buffer.

9. An implantable medical device comprising:
   a monitoring element configured to sense one or more signals associated with a plurality of neurological events that include ictal content;
   a memory component configured to store a plurality of data records in a data structure and replace some of the data records of the plurality of data records stored on the data structure as new data records of the plurality of data records are received in the memory component, the plurality of data records associated with the neurological events and include the ictal content; and
   a processing component, the processing component configured to detect the neurological events, create a data record of each neurological event and store a plurality of the data records in the memory component, determine a priority index for the plurality of data records based on severity levels of the detected neurological events, where the severity levels are based on analysis of the ictal content and where the priority index is higher for a higher severity level, and selectively replace an existing data record of the plurality of data records on the data structure with a newer data record having a higher priority index than the existing data record when the data structure is full.

10. The device of claim 9, wherein the processing component is configured to determine the severity levels of the neurological events based on a duration of the detected neurological events.

11. The device of claim 9, wherein the processing component is configured to determine the severity levels of the neurological events based on a peak ratio of foreground to background ictal content of the neurological events.

12. The device of claim 9, wherein the processing component is configured to determine the severity levels of the neurological events based on a spread of ictal content of the detected neurological events.

13. The device of claim 9, wherein the neurological events comprise seizures.

14. The device of claim 9, wherein the memory component comprises a circular buffer that contains the plurality of data records.

15. An implantable medical device comprising:
   means for sensing a neurological event that includes ictal content;
   means for creating a data record of the neurological event that includes the ictal content;
   means for determining a severity level of the neurological event based on analysis of the ictal content;
   means for storing the data record in a data structure containing a plurality of data records, the plurality of data records representing information about a plurality of neurological events;
   means for determining a priority index for the plurality of data records based on severity levels of the determined neurological events where the priority index is higher for a higher severity level; and
   means for selectively replacing an existing data record in the data structure with a newer data record that has a higher priority index when the data structure is full.

* * * * *